(12) United States Patent
Bakos et al.

(10) Patent No.: US 10,905,424 B2
(45) Date of Patent: Feb. 2, 2021

(54) CURVED TIP SURGICAL STAPLER BUTTRESS ASSEMBLY APPLICATOR WITH PROXIMAL ALIGNMENT FEATURES

(71) Applicant: Ethicon LLC, Guaynabo, PR (US)

(72) Inventors: Gregory J. Bakos, Mason, OH (US); Jason L. Harris, Lebanon, OH (US); Pamela M. Ridgley, Lebanon, OH (US); Frederick E. Shelton, IV, Hillsboro, OH (US); Michael J. Vendely, Lebanon, OH (US); Mark S. Zeiner, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 48 days.

(21) Appl. No.: 16/235,670

(22) Filed: Dec. 28, 2018

(65) Prior Publication Data

US 2020/0205827 A1    Jul. 2, 2020

(51) Int. Cl.
  *A61B 17/072*  (2006.01)
  *A61B 17/068*  (2006.01)
  *A61B 17/29*  (2006.01)

(52) U.S. Cl.
  CPC .... *A61B 17/07292* (2013.01); *A61B 17/0682* (2013.01); *A61B 17/072* (2013.01);
  (Continued)

(58) Field of Classification Search
  CPC .............. A61B 17/068; A61B 17/0644; A61B 17/0686; A61B 17/072; A61B 17/07207; A61B 17/07292; A61B 17/115; A61B 2017/07214; A61B 2017/07278; A61B 2017/07271; A61B 2017/2927
  (Continued)

(56) References Cited

U.S. PATENT DOCUMENTS 4,805,823 A  2/1989 Rothfuss
5,415,334 A  5/1995 Williamson, IV et al.
(Continued)

FOREIGN PATENT DOCUMENTS

EP  3 597 120 A1  1/2020

OTHER PUBLICATIONS

U.S. Appl. No. 16/234,727, entitled "Surgical Stapler with Tissue Engagement Features Around Tissue Containment Pin," filed Dec. 28, 2018.
(Continued)

*Primary Examiner* — Scott A Smith
(74) *Attorney, Agent, or Firm* — Frost Brown Todd LLC

(57) ABSTRACT

A buttress applier cartridge assembly includes buttress assemblies and a buttress applier cartridge for use with an end effector of a surgical stapler. The buttress assemblies each include a buttress to support a staple formed therein as well an adhesive for adhering to the end effector. The buttress applier cartridge includes a housing, a platform that extends longitudinally and supports the buttress assemblies, and an opening to accommodate a curved tip of the end effector when clamping the end effector onto the platform to transfer the buttress assemblies to the end effector. A proximal alignment feature of the buttress applier cartridge contacts the end effector to align the end effector with the buttress assemblies prior to attaching the buttress assemblies to the end effector.

20 Claims, 31 Drawing Sheets

(52) U.S. Cl.
    CPC ...... *A61B 17/07207* (2013.01); *A61B 17/068* (2013.01); *A61B 2017/0688* (2013.01); *A61B 2017/07214* (2013.01); *A61B 2017/07221* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/2945* (2013.01)

(58) Field of Classification Search
    USPC .. 227/19, 175.1, 176.1, 175.2, 178.1, 180.1; 606/1, 139, 153, 215, 219
    See application file for complete search history.

(56) References Cited

U.S. PATENT DOCUMENTS

| | | |
|---|---|---|
| 5,465,895 A | 11/1995 | Knodel et al. |
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,752,965 A * | 5/1998 | Francis ............ A61B 17/07207 227/178.1 |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 5,902,312 A * | 5/1999 | Frater ............ A61B 17/07207 606/148 |
| 6,231,565 B1 | 5/2001 | Tovey et al. |
| 6,364,888 B1 | 4/2002 | Niemeyer et al. |
| 6,638,285 B2 * | 10/2003 | Gabbay ................ A61B 17/072 606/139 |
| 6,783,524 B2 | 8/2004 | Anderson et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,134,587 B2 | 11/2006 | Schwemberger et al. |
| 7,143,923 B2 | 12/2006 | Shelton, IV et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney et al. |
| 7,644,848 B2 | 1/2010 | Swayze et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 8,011,550 B2 * | 9/2011 | Aranyi ............ A61B 17/07207 227/175.1 |
| 8,091,756 B2 * | 1/2012 | Viola ............... A61B 17/07207 227/178.1 |
| 8,141,762 B2 | 3/2012 | Bedi et al. |
| 8,210,411 B2 | 7/2012 | Yates et al. |
| 8,365,972 B2 * | 2/2013 | Aranyi ................ A61B 17/068 227/175.1 |
| 8,371,491 B2 | 2/2013 | Huitema et al. |
| 8,371,493 B2 * | 2/2013 | Aranyi ............ A61B 17/07292 227/176.1 |
| 8,408,439 B2 | 4/2013 | Huang et al. |
| 8,453,904 B2 * | 6/2013 | Eskaros ............... A61B 17/072 227/175.1 |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,579,990 B2 | 11/2013 | Priewe |
| 8,584,920 B2 * | 11/2013 | Hodgkinson ...... A61B 17/0682 227/175.1 |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,870,050 B2 * | 10/2014 | Hodgkinson ...... A61B 17/0682 227/175.1 |
| 8,899,464 B2 | 12/2014 | Hueil et al. |
| 8,992,060 B2 | 4/2015 | Dassanayake et al. |
| 8,998,060 B2 | 4/2015 | Bruewer et al. |
| 9,050,084 B2 * | 6/2015 | Schmid ............ A61B 17/07207 |
| 9,101,359 B2 | 8/2015 | Smith et al. |
| 9,186,142 B2 | 11/2015 | Fanelli et al. |
| 9,198,644 B2 | 12/2015 | Balek et al. |
| 9,198,662 B2 * | 12/2015 | Barton ............ A61B 17/07207 |
| 9,211,120 B2 | 12/2015 | Scheib et al. |
| 9,220,500 B2 * | 12/2015 | Swayze ............ A61B 17/07292 |
| 9,301,759 B2 | 4/2016 | Spivey et al. |
| 9,386,984 B2 * | 7/2016 | Aronhalt .......... A61B 17/07207 |
| 9,393,018 B2 | 7/2016 | Wang et al. |
| 9,398,911 B2 | 7/2016 | Auld et al. |
| 9,433,420 B2 * | 9/2016 | Hodgkinson .... A61B 17/07207 |
| 9,492,170 B2 | 11/2016 | Bear et al. |
| 9,517,065 B2 | 12/2016 | Simms et al. |
| 9,597,082 B2 | 3/2017 | Stokes et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,848,871 B2 | 12/2017 | Harris et al. |
| 9,867,615 B2 | 1/2018 | Fanelli et al. |
| 9,913,642 B2 | 3/2018 | Leimbach et al. |
| 9,936,954 B2 | 4/2018 | Shelton, IV et al. |
| 9,999,408 B2 | 6/2018 | Boudreaux et al. |
| 10,045,780 B2 | 8/2018 | Adams et al. |
| 10,092,292 B2 | 10/2018 | Boudreaux et al. |
| D833,010 S | 11/2018 | Harris et al. |
| 10,123,798 B2 | 11/2018 | Baxter, III et al. |
| D836,198 S | 12/2018 | Harris et al. |
| D836,199 S | 12/2018 | Schowalter et al. |
| 10,349,939 B2 | 7/2019 | Shelton, IV et al. |
| 2003/0120284 A1 | 6/2003 | Palacios et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2006/0004407 A1 * | 1/2006 | Hiles ................ A61B 17/0644 606/215 |
| 2007/0246505 A1 * | 10/2007 | Pace-Floridia ....... A61L 31/044 227/175.1 |
| 2008/0169328 A1 | 7/2008 | Shelton |
| 2009/0277944 A9 * | 11/2009 | Dalessandro .... A61B 17/07207 227/154 |
| 2012/0241493 A1 | 9/2012 | Baxter, III et al. |
| 2013/0068816 A1 | 3/2013 | Vasudevan et al. |
| 2013/0075447 A1 | 3/2013 | Weisenburgh et al. |
| 2013/0206813 A1 | 8/2013 | Nalagatla |
| 2014/0239037 A1 | 8/2014 | Boudreaux et al. |
| 2015/0351758 A1 | 12/2015 | Shelton, IV et al. |
| 2016/0089146 A1 | 3/2016 | Harris et al. |
| 2016/0278774 A1 | 9/2016 | Shelton, IV et al. |
| 2017/0027571 A1 | 2/2017 | Nalagatla et al. |
| 2017/0049444 A1 | 2/2017 | Schellin et al. |
| 2017/0055980 A1 | 3/2017 | Vendely et al. |
| 2017/0055981 A1 | 3/2017 | Vendely et al. |
| 2017/0055982 A1 | 3/2017 | Zeiner et al. |
| 2017/0055986 A1 | 3/2017 | Harris et al. |
| 2017/0056016 A1 | 3/2017 | Barton et al. |
| 2017/0056017 A1 | 3/2017 | Vendely et al. |
| 2017/0056018 A1 | 3/2017 | Zeiner et al. |
| 2017/0086823 A1 | 3/2017 | Leimbach et al. |
| 2017/0086837 A1 | 3/2017 | Vendely et al. |
| 2017/0086842 A1 | 3/2017 | Shelton, IV et al. |
| 2018/0235610 A1 | 8/2018 | Harris et al. |

(56) References Cited

U.S. PATENT DOCUMENTS

2018/0235611 A1 8/2018 Harris et al.
2018/0235619 A1 8/2018 Harris et al.
2018/0235626 A1 8/2018 Shelton, IV et al.
2019/0000481 A1 1/2019 Harris et al.

OTHER PUBLICATIONS

U.S. Appl. No. 16/234,740, entitled "Surgical Stapler with Sloped Staple Deck for Varying Tissue Compression," filed Dec. 28, 2018.
U.S. Appl. No. 16/235,473, entitled "Adhesive Distribution on Buttress for Surgical Stapler," filed Dec. 28, 2018.
U.S. Appl. No. 16/235,488, entitled "Configuration of Buttress for Surgical Stapler," filed Dec. 28, 2018.
U.S. Appl. No. 16/235,503, entitled "Surgical Stapler Buttress with Tissue In-Growth Promotion," filed Dec. 28, 2018.
U.S. Appl. No. 16/235,522, entitled "Applicator for Surgical Stapler Buttress," filed Dec. 28, 2018.
U.S. Appl. No. 16/235,541, entitled "Packaging for Surgical Stapler Buttress," filed Dec. 28, 2018.
U.S. Appl. No. 16/235,617, entitled "Method of Applying Buttresses to Surgically Cut and Stapled Sites," filed Dec. 28, 2018.
U.S. Appl. No. 16/235,630, entitled "Curved Tip Surgical Stapler Buttress Assembly Applicator with Opening Feature for Curved Tip Alignment," filed Dec. 28, 2018.
U.S. Appl. No. 16/235,681, entitled "Curved Tip Surgical Buttress Assembly Applicator with Compression Layer Pocket Features," filed Dec. 28, 2018.
Design U.S. Appl. No. 29/675,045, entitled "Surgical Stapler Deck with Tissue Engagement Cleat Features," filed Dec. 28, 2018.
Design U.S. Appl. No. 29/675,047, entitled "Surgical Stapler Deck with Tissue Engagement Recess Features," filed Dec. 28, 2018.
Design U.S. Appl. No. 29/675,168, entitled "Applicator for Surgical Stapler Buttress," filed Dec. 28, 2018.
Design U.S. Appl. No. 29/675,170, entitled "Buttress for Surgical Stapler," filed Dec. 28, 2018.
Design U.S. Appl. No. 29/675,172, entitled "Tray for Surgical Stapler Buttress Applicator," filed Dec. 28, 2018.
Design U.S. Appl. No. 29/675,197, entitled "Applicator for a Stapler Buttress," filed Dec. 28, 2018.
Design U.S. Appl. No. 29/675,199, entitled "Buttress Assembly for a Surgical Stapler," filed Dec. 28, 2018.
U.S. Appl. No. 62/209,041, entitled "Method and Apparatus for Applying a Buttress to End Effector of a Surgical Stapler," filed Aug. 24, 2015.
European Search Report, Extended, and Written Opinion dated Apr. 1, 2020 for Application No. EP 19219391.0, 9 pgs.
International Search Report and Written Opinion dated Apr. 1, 2020 for Application No. PCT/IB2019/060820, 14 pgs.

\* cited by examiner

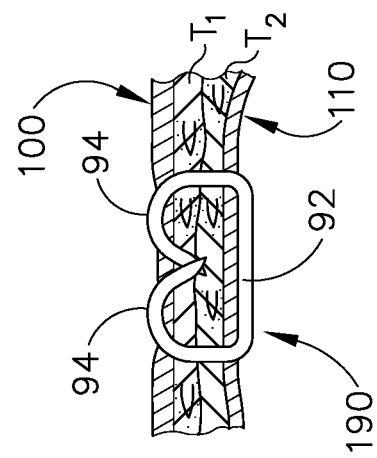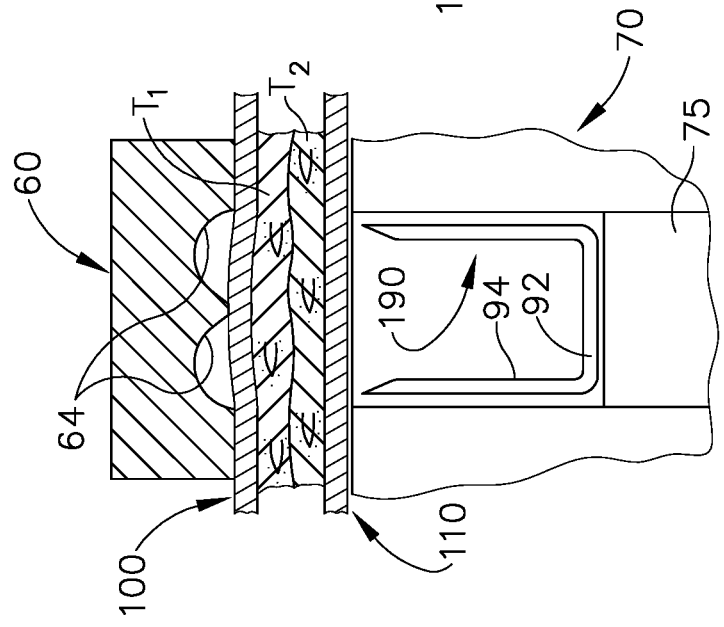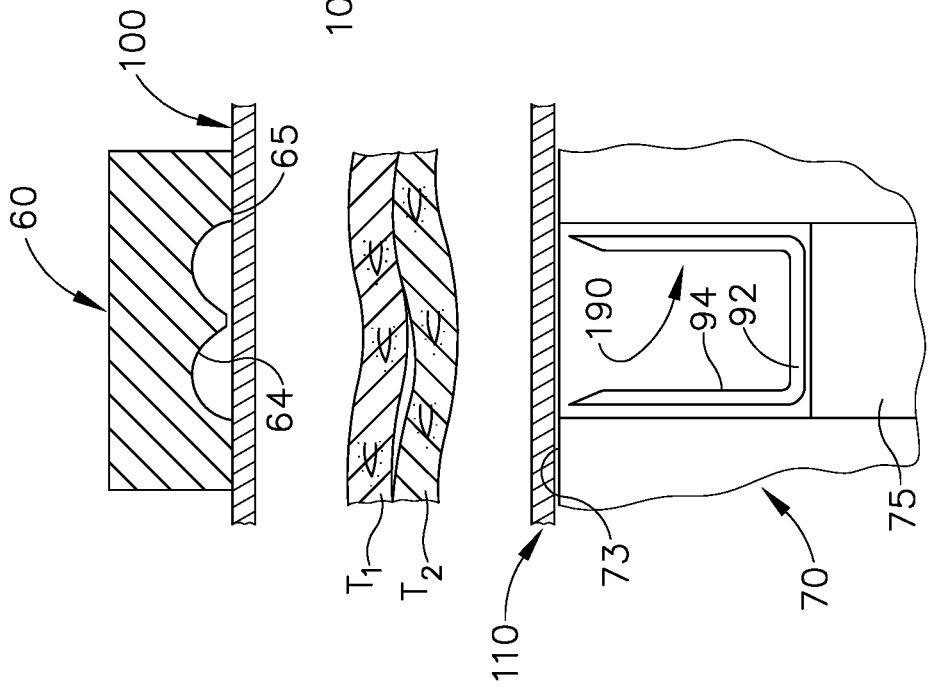

CURVED TIP SURGICAL STAPLER BUTTRESS ASSEMBLY APPLICATOR WITH PROXIMAL ALIGNMENT FEATURES

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Pat. No. 9,186,142, entitled "Surgical Instrument End Effector Articulation Drive with Pinion and Opposing Racks," issued Nov. 17, 2015; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,839,421, entitled "Jaw Closure Feature for End Effector of Surgical Instrument," issued Dec. 12, 2017; U.S. Pat. No. 9,867,615, entitled "Surgical Instrument with Articulation Lock having a Detenting Binary Spring," issued Jan. 16, 2018; U.S. Pat. No. 9,622,746, entitled "Distal Tip Features for End Effector of Surgical Instrument," issued Apr. 18, 2017; U.S. Pat. No. 10,092,292, entitled "Staple Forming Features for Surgical Stapling Instrument," issued Oct. 9, 2018; U.S. Pat. No. 9,795,379, entitled "Surgical Instrument with Multi-Diameter Shaft," issued Oct. 24, 2017; and U.S. Pat. No. 9,808,248, entitled "Installation Features for Surgical Instrument End Effector Cartridge," issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pat. No. 9,597,082, entitled "Method and Apparatus for Sealing End-to-End Anastomosis" issued Mar. 21, 2017; U.S. Pat. No. 9,398,911, entitled "Rotary Powered Surgical Instruments with Multiple Degrees of Freedom," issued Jul. 26, 2016; U.S. Pat. Pub. No. 2013/0206813, entitled "Linear Stapler," published Aug. 15, 2013, now abandoned; U.S. Pat. Pub. No. 2008/0169328, entitled "Buttress Material for Use with a Surgical Stapler," published Jul. 17, 2008, now abandoned; U.S. Pat. No. 9,848,871, entitled "Woven and Fibrous Materials for Reinforcing a Staple Line," issued Dec. 26, 2017; U.S. Pat. No. 9,936,954, entitled "Devices and Methods for Sealing Staples in Tissue" issued Apr. 10, 2018; and U.S. Pat. Pub. No. 2016/0089146, entitled "Circular Fastener Cartridges for Applying Radially Expandable Fastener Lines" published Mar. 31, 2016, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 17A depicts a cross-sectional end view of a portion of the end effector of FIG. 15 with the buttress assembly of FIG. 15 applied to the end effector, with tissue positioned between the buttresses in the end effector, and with the anvil in an open position;

FIG. 17B depicts a cross-sectional end view of the combined end effector and buttress assembly of FIG. 17A, with tissue positioned between the buttresses in the end effector, and with the anvil in a closed position;

FIG. 17C depicts a cross-sectional view of a staple and the buttress assembly of FIG. 17A having been secured to the tissue by the end effector of FIG. 15;

Figure 1:
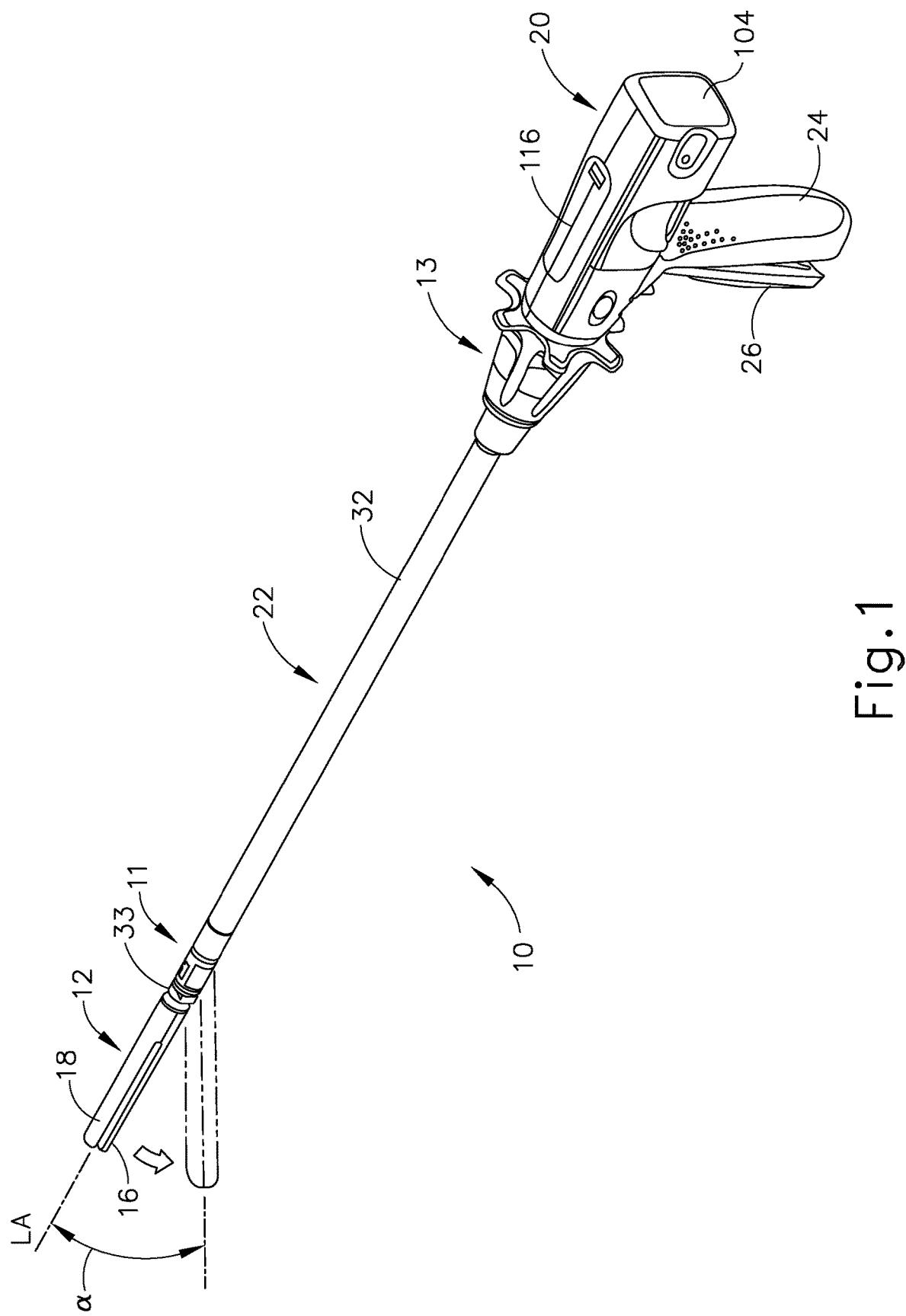
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. EXEMPLARY SURGICAL STAPLER

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical," "horizontal," "upper," and "lower" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In the present example, anvil (18) can also be considered an upper jaw. Furthermore, in some versions like the present example, the upper jaw or anvil (18) pivots with respect to a stationary lower jaw (16); however, in some other versions the upper jaw or anvil (18) is stationary while the lower jaw (16) pivots. In some versions, lower jaw (16) is constructed in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; and/or at least some of the teachings of U.S. Pat. No. 10,092,292, entitled "Staple Forming Features for Surgical Stapling Instrument," issued Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein. Other suitable forms that firing beam (14) may take will be apparent to those of ordinary skill in the art in view of the teachings herein.

Figure 3:
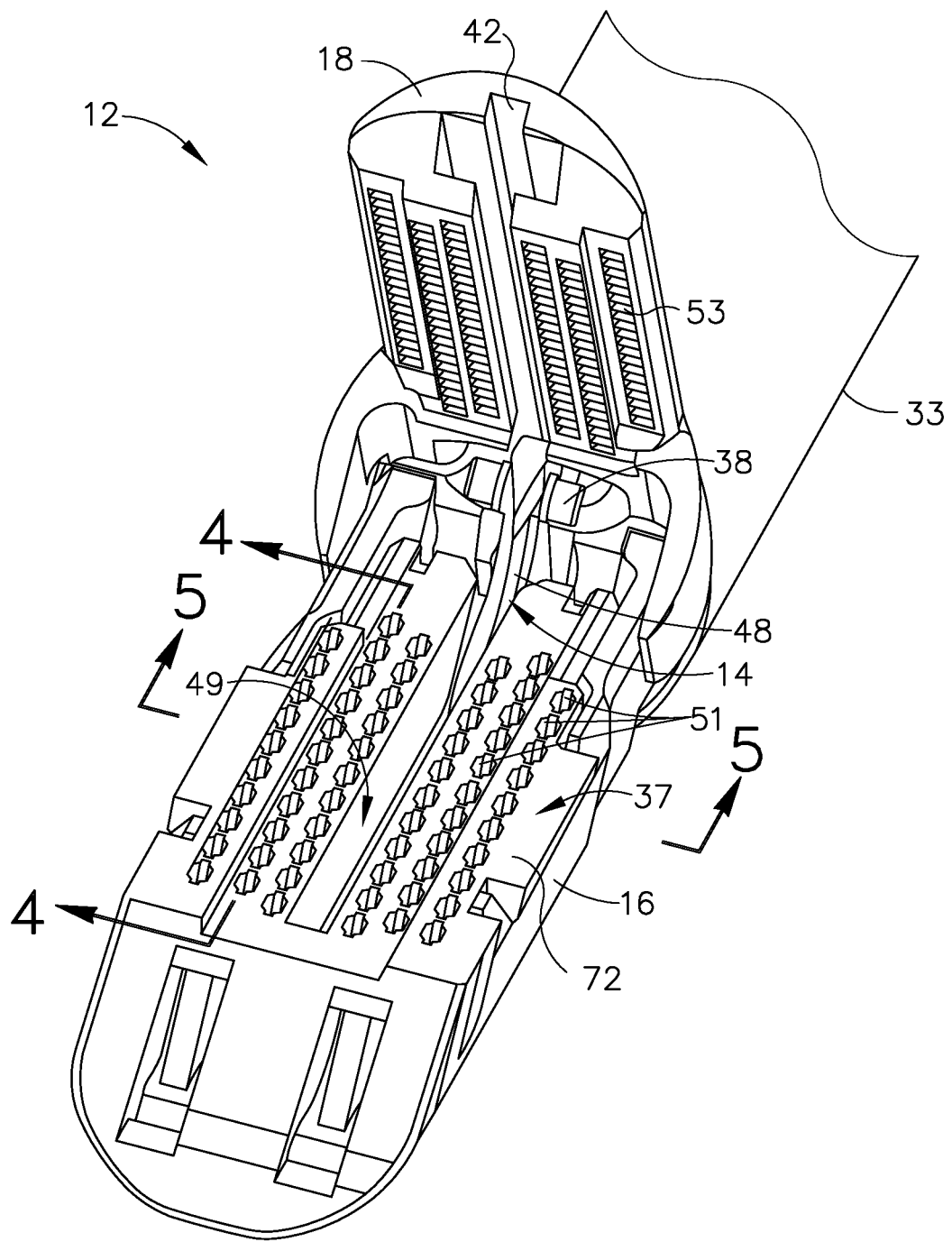
FIG. 3 depicts a perspective view of an opened end effector of the instrument of FIG. 1.
Figure 4A:
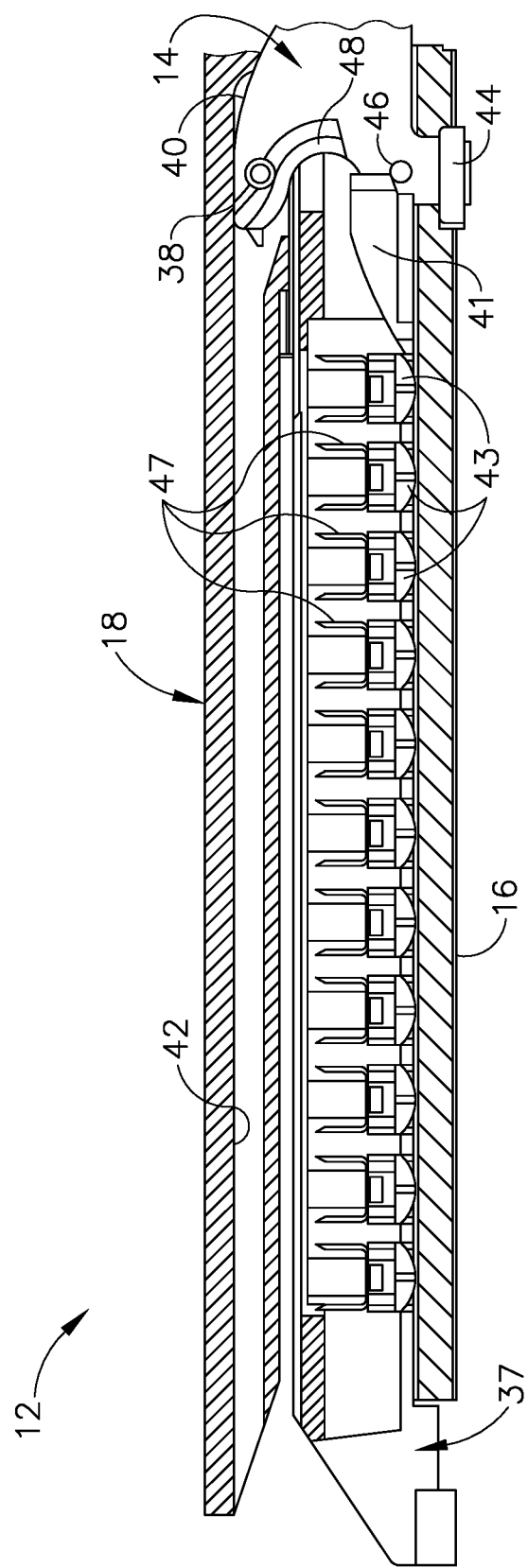
FIG. 4A depicts a side cross-sectional view of the end effector of FIG. 3, taken along line 4-4 of FIG. 3, with the firing beam in a proximal position.
Figure 4B:
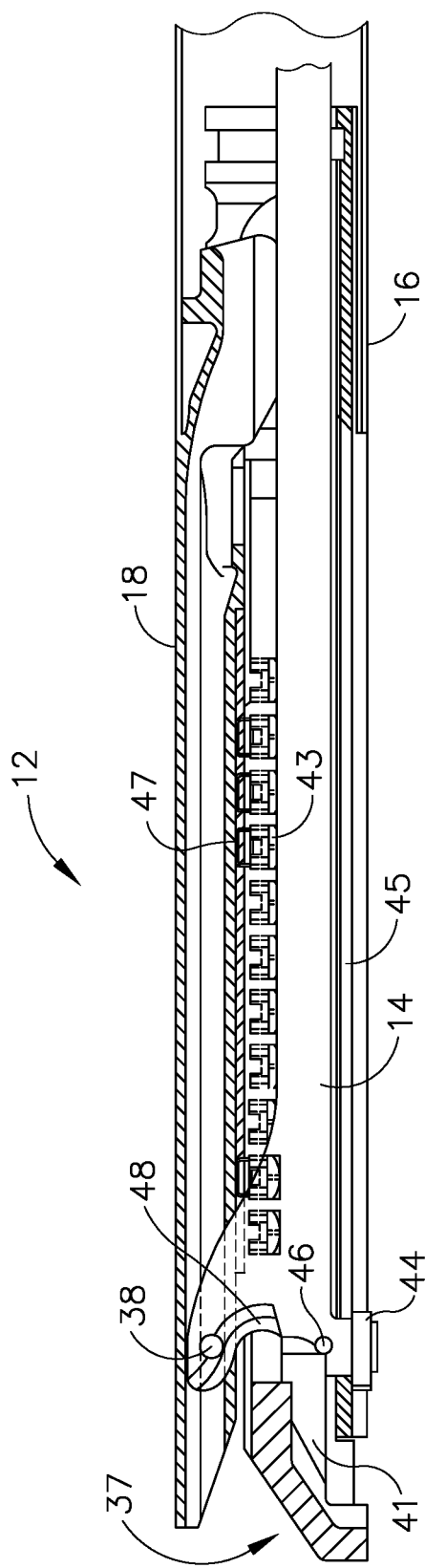
FIG. 4B depicts a side cross-sectional view of the end effector of FIG. 3, taken along line 4-4 of FIG. 3, with the firing beam in a distal position.
Figure 5:
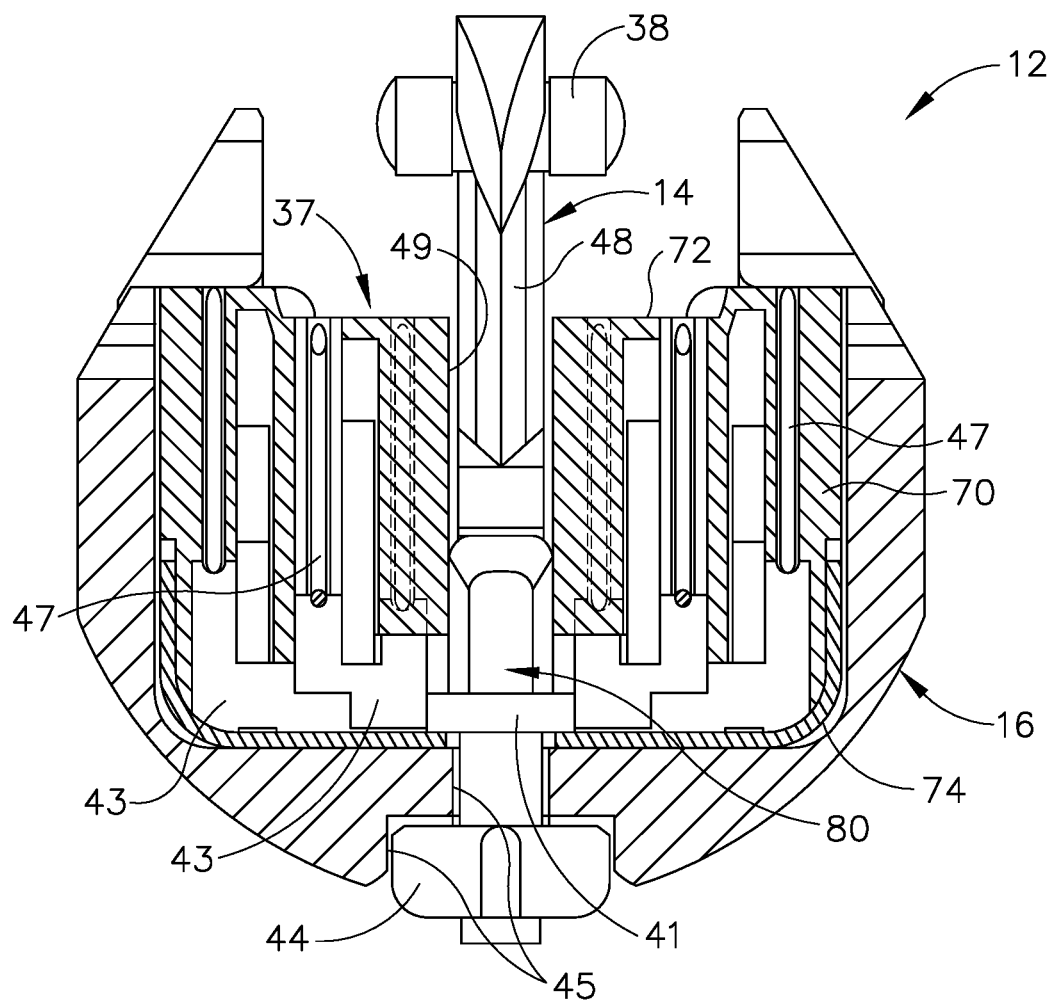
FIG. 5 depicts an end cross-sectional view of the end effector of FIG. 3, taken along line 5-5 of FIG. 3.
Figure 6:
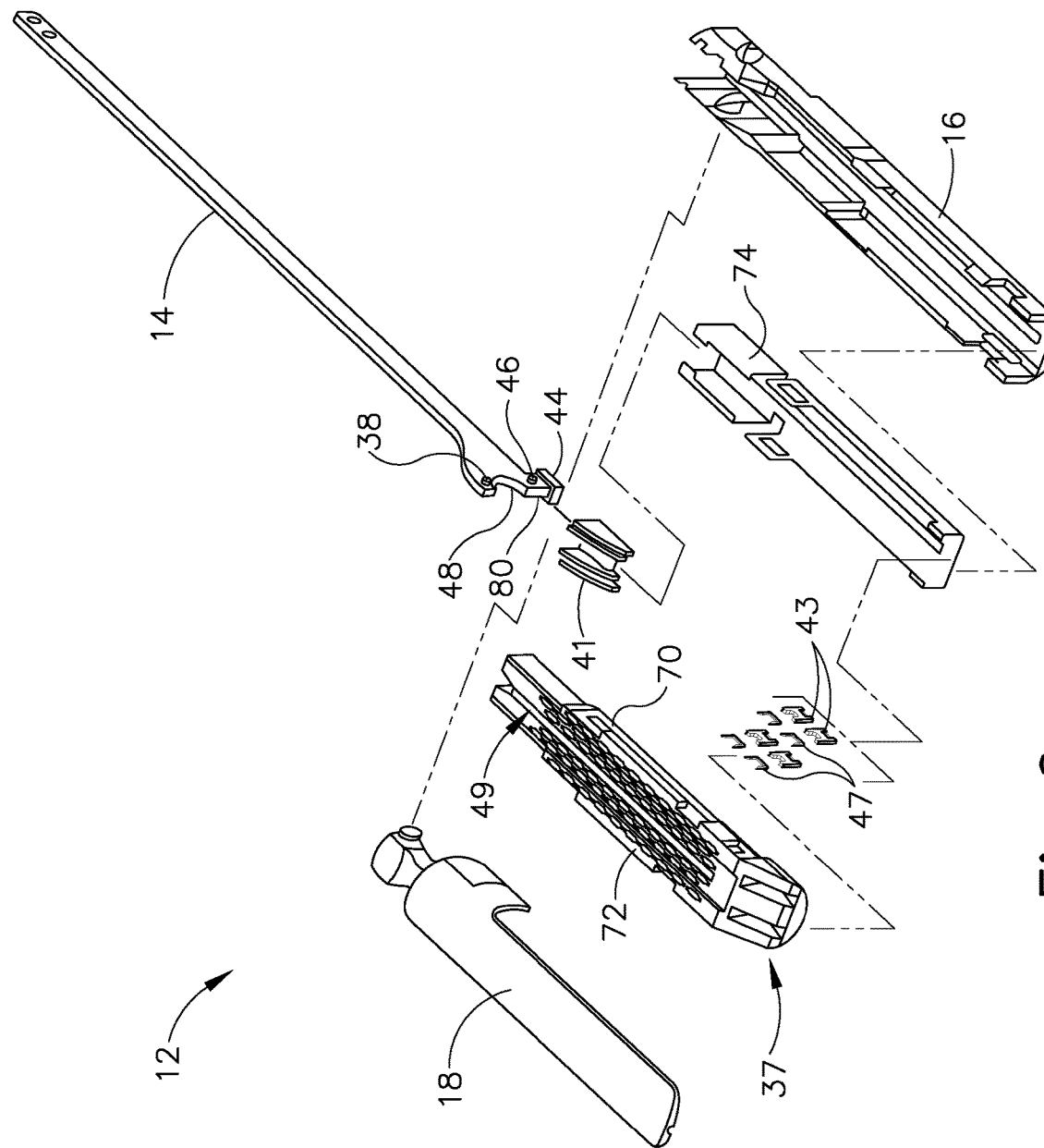
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14) and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
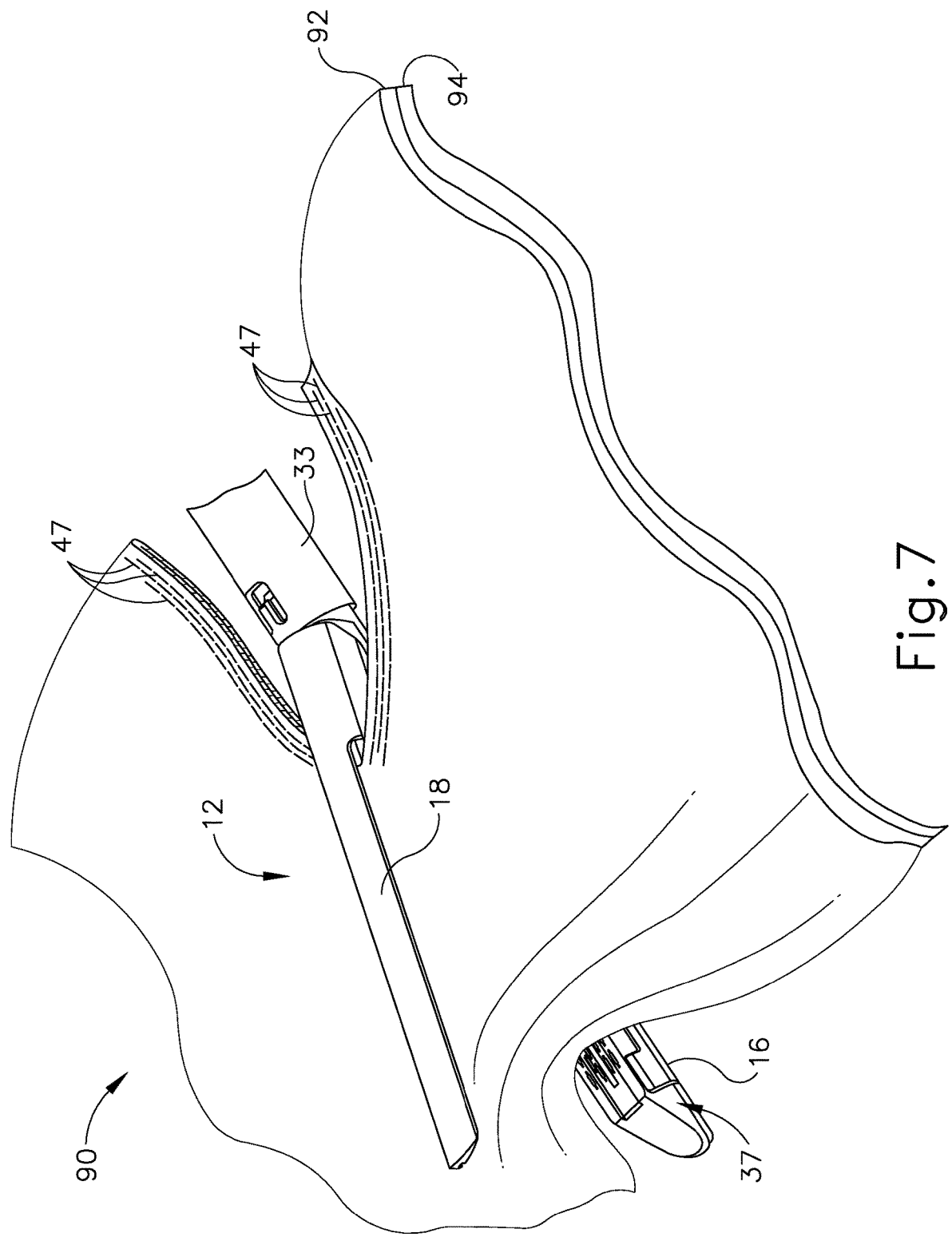
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY END EFFECTOR WITH VISUALIZATION, LEAD-IN, AND GATHERING FEATURE

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
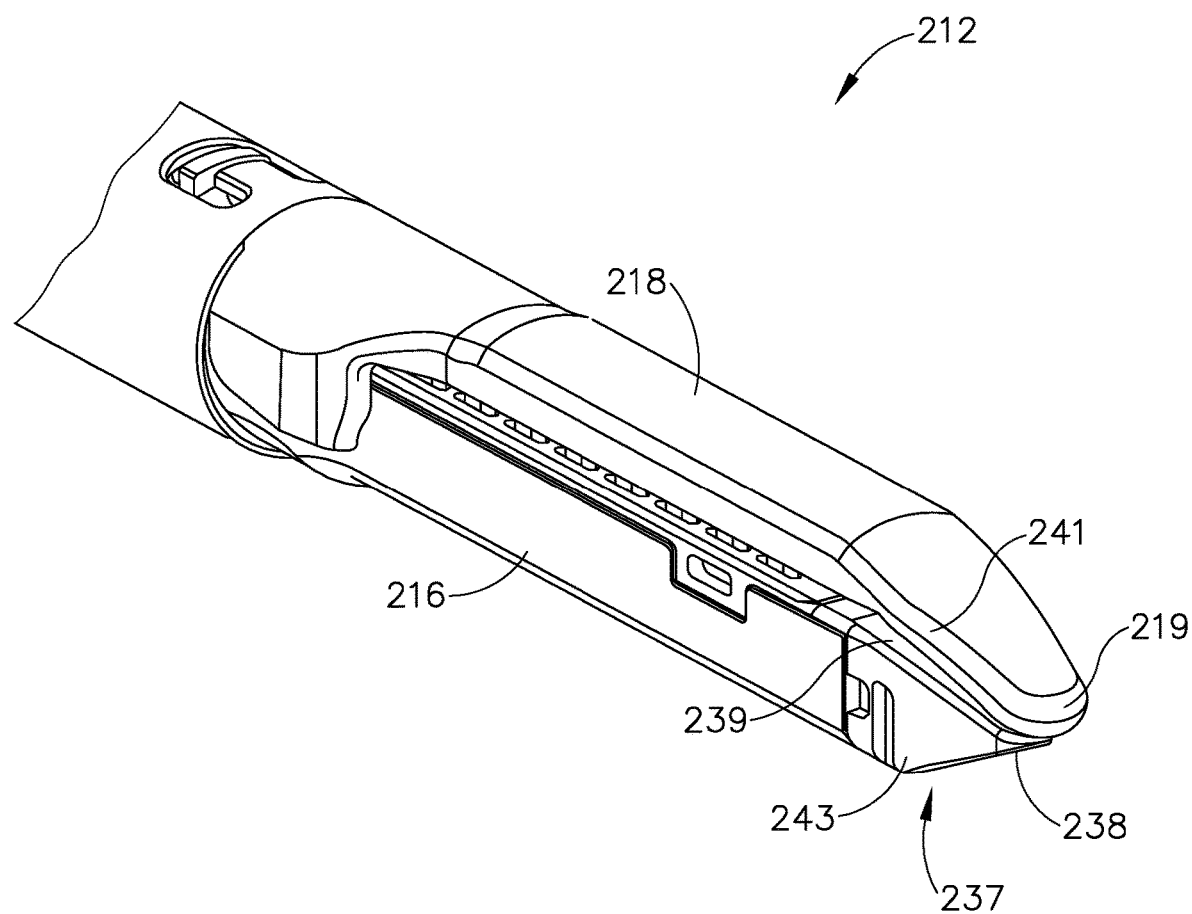
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
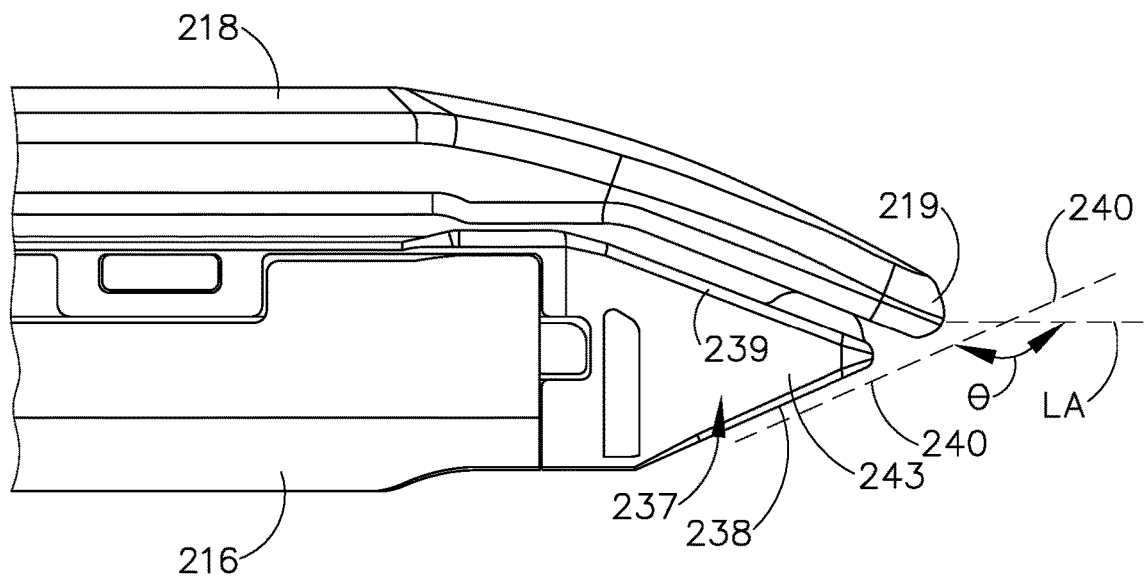
FIG. 9 depicts an enlarged, side view of the end effector of FIG. 8.
Figure 10:
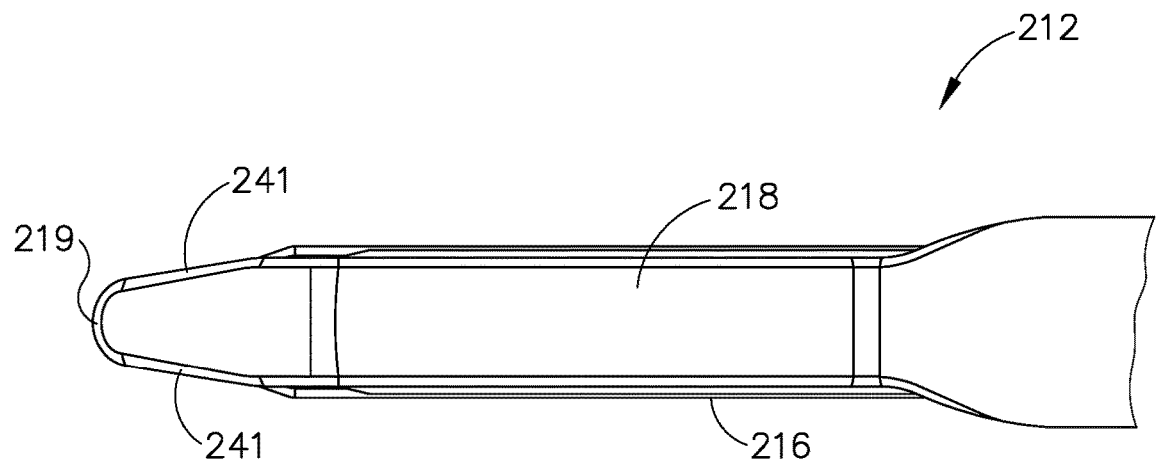
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle ($\theta$).

Viewing angle ($\theta$) may establish the relative visibility that a user has regarding distal tip (219). In particular, the user can see in front of distal tip (219) along any line of sight that passes through the intersection of sight line (240) and longitudinal axis (LA) within viewing angle ($\theta$). For instance, as viewing angle ($\theta$) increases, the user would have greater visibility of the area immediately in front of distal tip (219) from proximal vantage points; whereas as viewing angle ($\theta$) decreases, the user has less visibility of the area in front of distal tip (219) from proximal vantage points. In some versions, viewing angle ($\theta$) defines an angle greater than 90 degrees. Additionally, in some versions, viewing angle ($\theta$) defines an angle greater than 135 degrees. Other suitable angles for viewing angle ($\theta$) will be apparent to one of ordinary skill in the art in view of the teachings herein. In the illustrated version, the user generally looks along sight line (240) or along some other line of sight within viewing angle ($\theta$), thus, the user has visibility along sight line as well as any area within viewing angle ($\theta$). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle ($\theta$) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," issued Oct. 9, 20018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

III. EXEMPLARY END EFFECTORS WITH BENT OR ANGLED ELASTICALLY DEFORMABLE ANVIL TIPS

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218)

may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
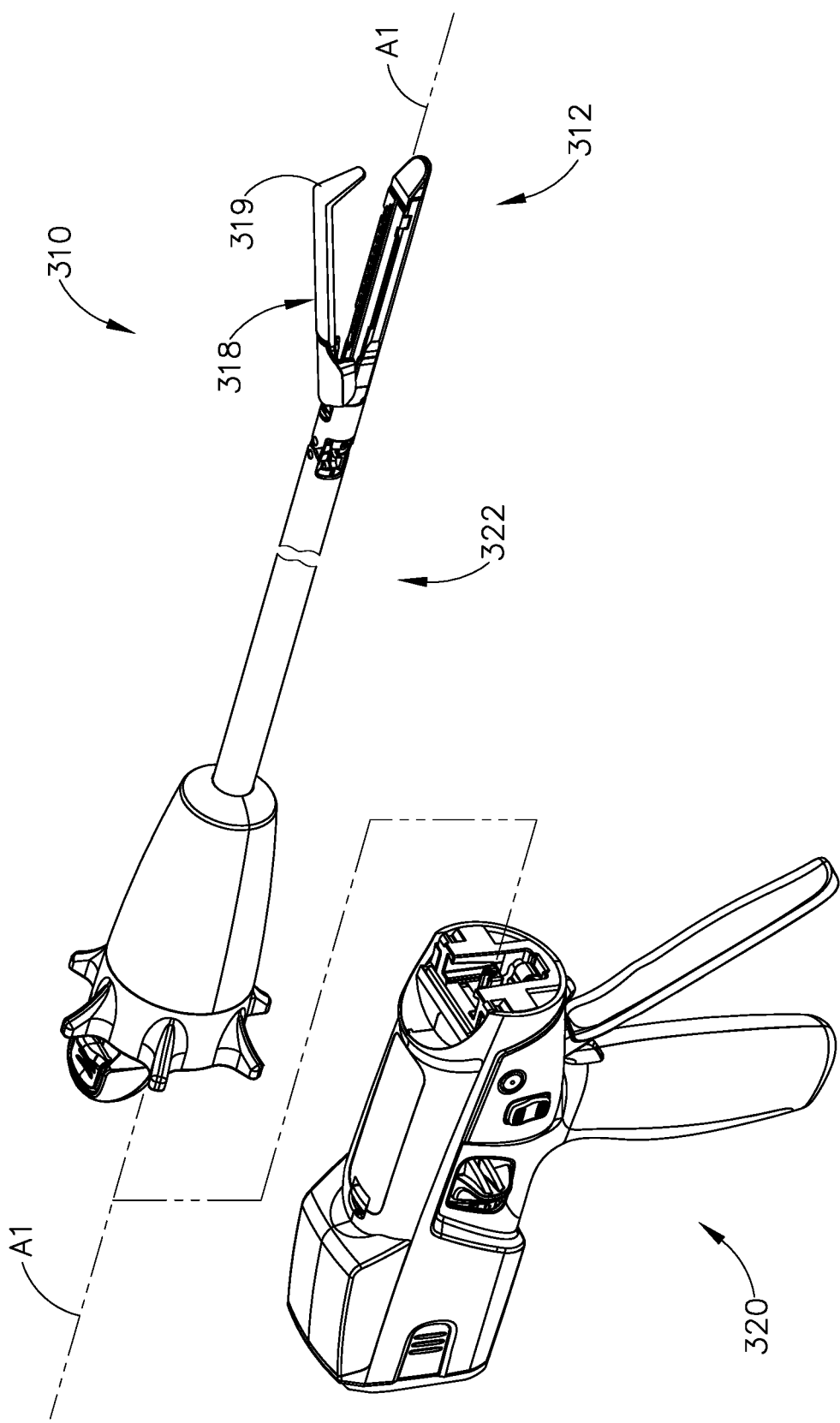
FIG. 11 depicts a perspective view of an exemplary surgical stapling instrument having an end effector with a bent or angled elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
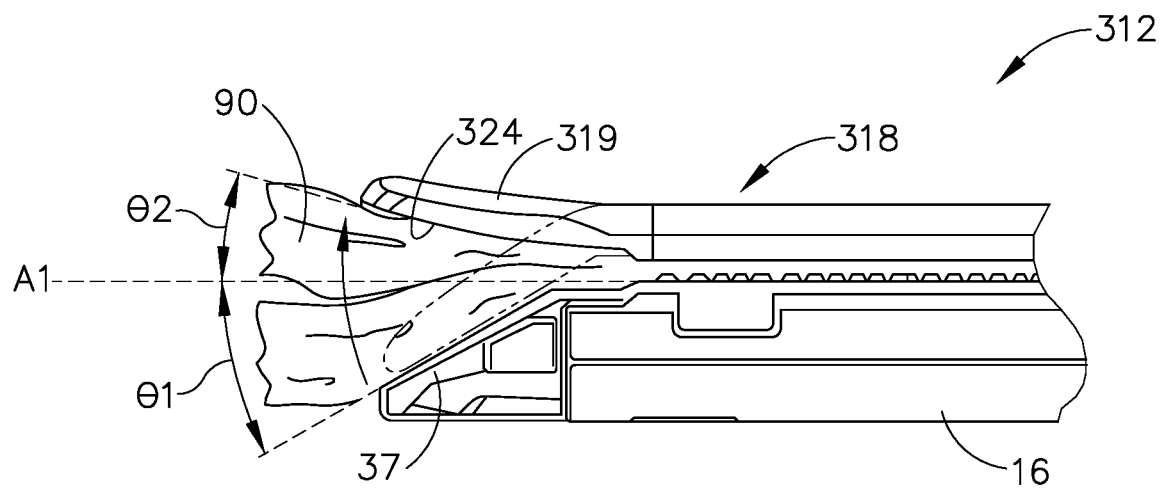
FIG. 12A depicts an enlarged side view of a distal portion of the end effector of FIG. 11.

FIG. 12A shows an enlarged side view of the distal end of end effector (312). End effector (312) comprises anvil (318) and lower jaw (16) that accepts cartridge (37) as described above with respect to instrument (10). Anvil (318) pivotably rotates toward lower jaw (16) in the same manner as anvil (18) as described above with respect to instrument (10). In this configuration, end effector (312) is similar to end effector (12), however, anvil (318) comprises angled distal tip (319) that is elastically deformable. As shown in FIG. 12A, tip (319) is imparted with a bias to an angled position that is shown in FIG. 11 and in phantom in FIG. 12A. Tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil (318) and lower jaw (16), tip (319) contacts cartridge (37). In this position, an underside surface (324) of tip (319) defines a plane that intersects a longitudinal axis (A1) defined by shaft (322) to form an angle (θ1). When closed and clamping tissue (90) between anvil (318) and lower jaw (16), underside surface (324) of tip (319) contacts tissue (90). In this position, underside surface (324) of tip (319) defines a plane that intersects longitudinal axis (A1) to form an angle (θ2). In the illustrated example of FIG. 12A, angles (θ1, θ2) are relative to longitudinal axis (A1), and the sum of angles (θ1, θ2) represent the range of motion distal tip (319) undergoes. By way of example only, and not limitation, in some examples angle (θ1) is between about 20 and about 70 degrees, or more particularly between about 30 degrees and about 50 degrees, in a downward direction from longitudinal axis (A1) toward cartridge (37). By way of example only, and not limitation, in some examples angle (θ2) is between about 0 and about 90 degrees in an upward direction from longitudinal axis (A1) away from cartridge (37). By way of example only, and not limitation, in some examples the range of motion undergone by tip (319) is between about 20 degrees and about 110 degrees. The angles described for angles (θ1, θ2) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
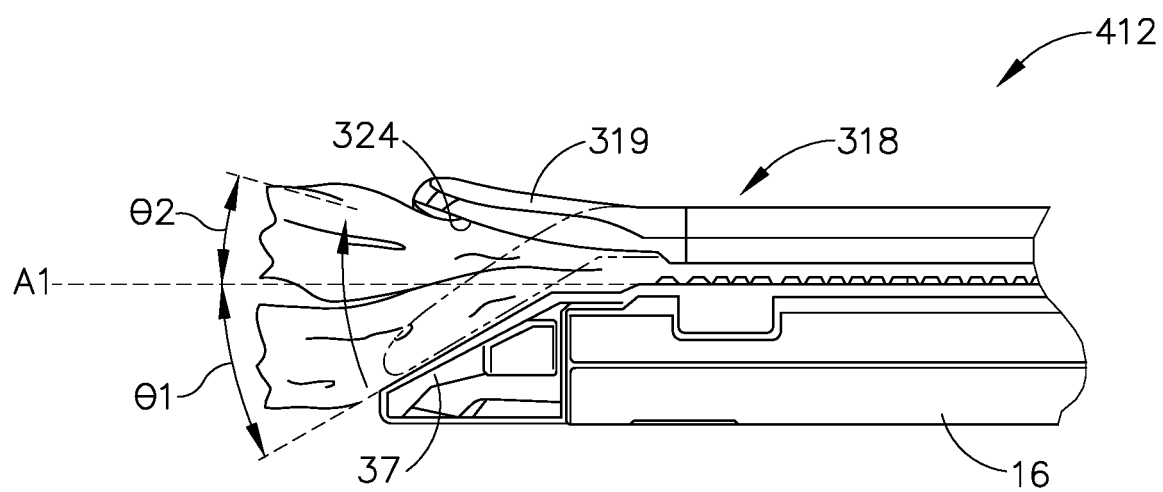
FIG. 12B depicts an enlarged side view of a distal portion of an alternate end effector similar to that of FIG. 11.

FIG. 12B shows another side view of an alternate end effector (412) similar to end effector (312) of FIG. 12A. With end effector (312), when anvil (318) is in its angled and non-deformed state (as seen in phantom in the view of FIG. 12A), anvil (318) extends to a point even with or proximal to the distal most end of cartridge (37). When anvil (318) is deformed such that it is deflected upwardly, the end of distal tip (319) extends to a point just distal to the distal most end of cartridge (37). With end effector (412), as shown in FIG. 12B, when anvil (318) is in its angled and non-deformed state (as seen in phantom in the view of FIG. 12B), anvil (318) extends to a point even with or proximal to the distal most end of cartridge (37). When anvil (318) is deformed such that it is deflected upwardly, the end of a distal tip (319) of anvil (318) extends to a point even with or proximal to the distal most end of cartridge (37). In this manner, anvil (318) of end effector (412) remains even with or proximal to the distal most end of cartridge (37) when anvil (318) is in its angled state or deformed state such that anvil (318) does not extend past the distal most end of cartridge (37) whether anvil (318) is in its angled and non-deformed state or in its deformed state. In some instances, this can be achieved by modifying anvil (318) such that distal tip (319) of anvil is shortened in length. In other instances, instruments (10, 310) may be modified to provide for a slight proximal retraction of anvil (318) when clamping. In view of the teachings herein, other ways to modify end effector (412) as it relates to control of anvil (318) position, will be apparent to those of ordinary skill in the art.

IV. ADDITIONAL EXEMPLARY END EFFECTORS FOR SURGICAL STAPLERS

Figure 13:
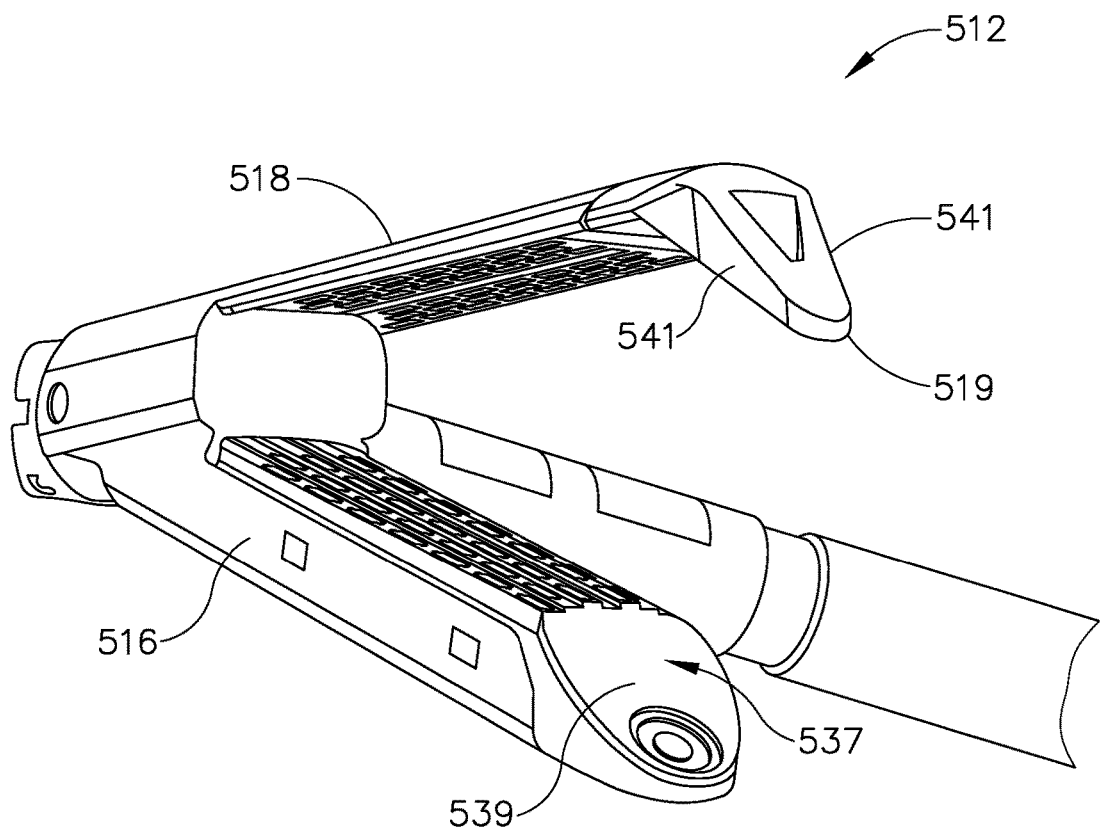
FIG. 13 depicts a perspective view of an alternative version of an end effector with an angled anvil and an angled cartridge.

FIG. 13 illustrates another exemplary end effector (512) that is configured for use with surgical stapling instruments as described herein. End effector (512) comprises an anvil (518) and a lower jaw (516). It will be appreciated that end effector (512) may be used in place of end effector (12) of instrument (10). End effector (512) may be integrally formed with instrument (10) or in the alternative may be interchangeable with end effector (12) of instrument (10).

Anvil (518) is operable to pivot relative to lower jaw (516). Anvil (518) and lower jaw (516) may clamp tissue (90) similarly to clamping performed by anvil (18) and lower jaw (16) shown in FIG. 1. End effector (512) further comprises a cartridge (537) operable to be placed in lower jaw (516) similarly to cartridge (37) shown in FIG. 3.

Anvil (518) has an elongated shape where the distal portion of anvil (518) angles toward cartridge (537), such that anvil (518) comprises a curved tip. The distal portion of anvil (518) angles toward cartridge (537) such that the distal most tip (519) of anvil (518) extends distally longitudinally further than cartridge (537). Though in some versions, distal tip (519) may extend to a distance longitudinally equal to cartridge (537) or proximal relative to the distal most point on cartridge (537). Furthermore, distal portion of anvil (518) includes sides (541) that taper as they approach the distal most tip (519) of anvil (518). This shape of anvil (518) may provide easier insertion of end effector (512) into a surgical site. For instance, the shape of anvil (518) may provide an atraumatic tissue deflection surface as anvil (518) contacts or moves through tissue. Such atraumatic tissue deflection may include urging tissue (e.g., a large vessel) proximally into the space between anvil (518) and lower jaw (516) as anvil (518) closes toward lower jaw (516). Once placed into a surgical site, the shape of anvil (518) may also provide better maneuverability of end effector (512) and better visibility of the distal end of end effector (512) in relation to anatomical structures at the surgical site. Other suitable variations of anvil (518) will be apparent to one of ordinary skill in the art in view of the teachings herein.

Cartridge (537) is operable to hold staples similar to staples (47) shown in FIG. 4A for driving into tissue. The distal end of cartridge (537) has a sloped profile. In particular, the distal end of cartridge (537) comprises an upper tapered surface (539), which leads to the distal most end of cartridge (537).

When tissue (90) is clamped between a closed cartridge (537) and anvil (518), the user can look to see where anvil (518) has clamped tissue (90). Furthermore, the user can determine whether the tissue is completely clamped between anvil (518) and cartridge (537) such that tissue does not spill over the end of end effector (512). The user may be able to also visualize the quality of the clamp between anvil (518) and cartridge (537) against tissue (90). It will be appreciated that in some instances, end effector (512) may be rotated before, during, or after clamping tissue (90). As a result, the shape of anvil (518) may also provide more accessible viewing of distal tip (519). The shape of anvil (518) and cartridge (537) may further promote easy insertion of end effector (512) into tissue in an atraumatic manner. Furthermore, it may be easier to fit end effector (512) through a trocar or other devices operable to introduce end effector (512) into a surgical site due to the tapered end of end effector (512). For instance, once distal tip (519) is fit into a trocar, the shape of anvil (518) may provide a lead-in, guiding the rest of end effector (512) into the trocar. In view of the teachings herein, those of ordinary skill in the art will further appreciate that visibility and maneuverability can be enhanced by the tapered design for both sides (541) of the distal portion of anvil (518).

Still referring to FIG. 13, by way of example only, and not limitation, in one example of end effector (512), the curved tip of anvil (518) may be configured as a dissecting tip for separating tissue. In some such versions, such dissection of tissue may be accomplished using the curved tip of anvil (518). In such instances, the curved tip of anvil (518) is a rigid structure without sharp cutting blades or surfaces and dissection occurs by the rigid curved tip separating and/or dissecting tissue that it contacts with sufficient force. In some versions where the curved tip of anvil (518) is configured as a dissecting tip, the tip of the dissecting tip terminates between the planes defined by the tissue contacting surface and the bottom surface. Also, the tip of the dissecting tip is spaced from a distal end of the cartridge when the end effector is in a closed position. In this manner, the curved tip is configured as a dissecting tip that can separate and/or dissect tissue without requiring engagement or interlocking of the anvil tip with the distal end of the cartridge. Also in this manner, the curved tip is configured as a dissecting tip having a shape such that a user can slide the tip behind certain tissue to separate and/or dissect the tissue it contacts when sufficient force is applied. Of course having the curved tip of anvil (518) configured as a dissecting tip is not required in all versions of anvil (518), and accordingly in other versions curved tip of anvil (518) can be an atraumatic tip or placement tip not configured to sever tissue as described above.

Figure 14:
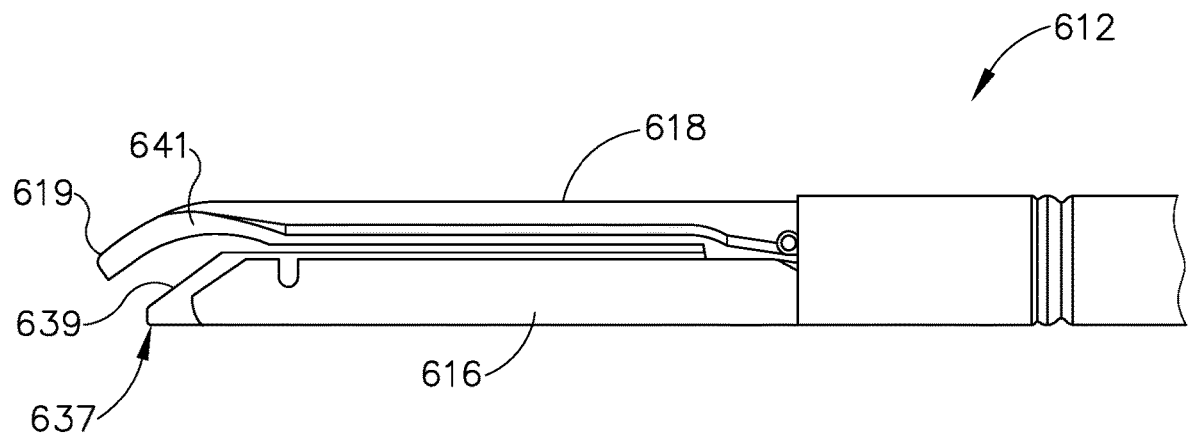
FIG. 14 depicts a perspective view of an alternative version of an end effector with an angled anvil and an angled cartridge.

FIG. 14 illustrates another exemplary end effector (612) that is configured for use with surgical stapling instruments as described herein. End effector (612) comprises an anvil (618) and a lower jaw (616). It will be appreciated that end effector (612) may be used in place of end effector (12) of instrument (10). End effector (612) may be integrally formed with instrument (10) or in the alternative may be interchangeable with end effector (12) of instrument (10).

Anvil (618) is operable to pivot relative to lower jaw (616). Anvil (618) and lower jaw (616) may clamp tissue (90) similarly to clamping performed by anvil (18) and lower jaw (16) shown in FIG. 1. End effector (612) further comprises a cartridge (637) operable to be placed in lower jaw (616) similarly to cartridge (37) shown in FIG. 3.

Anvil (618) has an elongated shape where the distal portion of anvil (618) angles toward cartridge (637). The distal portion of anvil (618) angles toward cartridge (637) such that the distal most tip (619) of anvil (618) extends distally longitudinally further than cartridge (637). Though in some versions, distal tip (619) may extend to a distance longitudinally equal to cartridge (637) or proximal relative to the distal most point on cartridge (637). Furthermore, distal portion of anvil (618) includes sides (641) that curve inward as they approach the distal most tip (619) of anvil (618). This shape of anvil (618) may provide easier insertion of end effector (612) into a surgical site. For instance, the shape of anvil (618) may provide an atraumatic tissue deflection surface as anvil (618) contacts or moves through tissue. Such atraumatic tissue deflection may include urging tissue (e.g., a large vessel) proximally into the space between anvil (618) and lower jaw (616) as anvil (618) closes toward lower jaw (616). Once placed into a surgical site, the shape of anvil (618) may also provide better maneuverability of end effector (612) and better visibility of the distal end of end effector (612) in relation to anatomical structures at the surgical site. Other suitable variations of anvil (618) will be apparent to one of ordinary skill in the art in view of the teachings herein.

Cartridge (637) is operable to hold staples similar to staples (47) shown in FIG. 4A for driving into tissue. The distal end of cartridge (637) has a sloped profile. In particular, the distal end of cartridge (637) comprises an upper tapered surface (639), which leads to the distal most end of cartridge (637).

When tissue (90) is clamped between a closed cartridge (637) and anvil (618), the user can look to see where anvil (618) has clamped tissue (90). Furthermore, the user can determine whether the tissue is completely clamped between anvil (618) and cartridge (637) such that tissue does not spill over the end of end effector (612). The user may be able to also visualize the quality of the clamp between anvil (618) and cartridge (637) against tissue (90). It will be appreciated that in some instances, end effector (612) may be rotated before, during, or after clamping tissue (90). As a result, the shape of anvil (618) may also provide more accessible viewing of distal tip (619). The shape of anvil (618) and cartridge (637) may further promote easy insertion of end effector (612) into tissue in an atraumatic manner. Furthermore, it may be easier to fit end effector (612) through a trocar or other devices operable to introduce end effector (612) into a surgical site due to the tapered end of end effector (612). For instance, once distal tip (619) is fit into a trocar, the shape of anvil (618) may provide a lead-in, guiding the rest of end effector (612) into the trocar. In view of the teachings herein, those of ordinary skill in the art will further appreciate that visibility and maneuverability can be enhanced by the curved design for both sides (641) of the distal portion of anvil (618).

In addition to the foregoing, end effectors (512, 612) and versions of instrument (10) incorporating end effectors (512, 612) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," issued Oct. 9, 20018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector (212) will be described in greater detail below.

V. EXEMPLARY BUTTRESS LOADING AND APPLICATION

Figure 15:
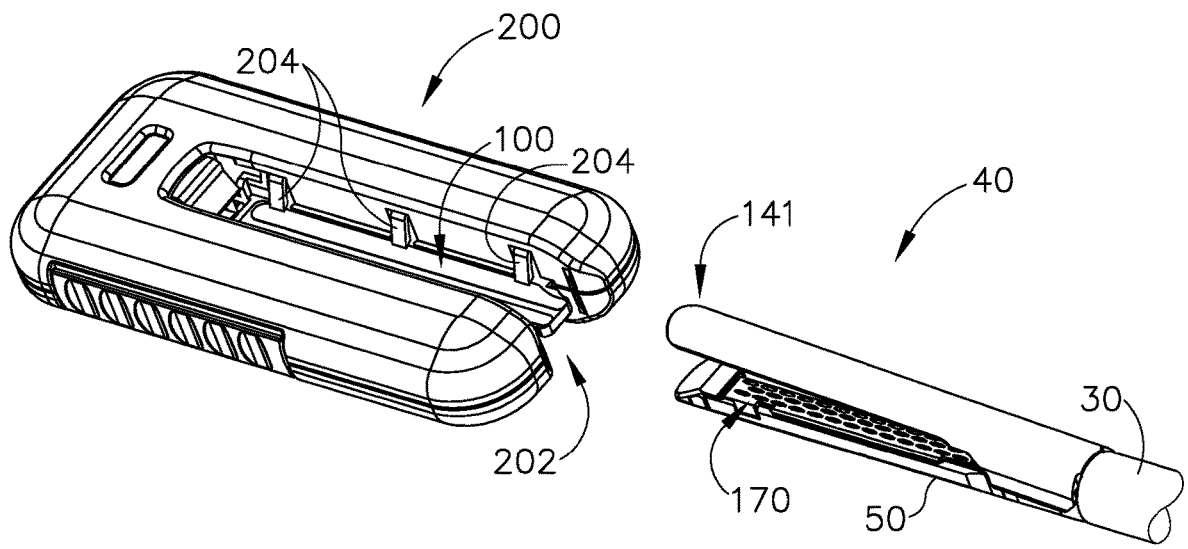
FIG. 15 depicts a perspective view of an exemplary end effector of a surgical stapler and an exemplary buttress assembly applicator, with the end effector approaching the buttress assembly applicator.
Figure 16:
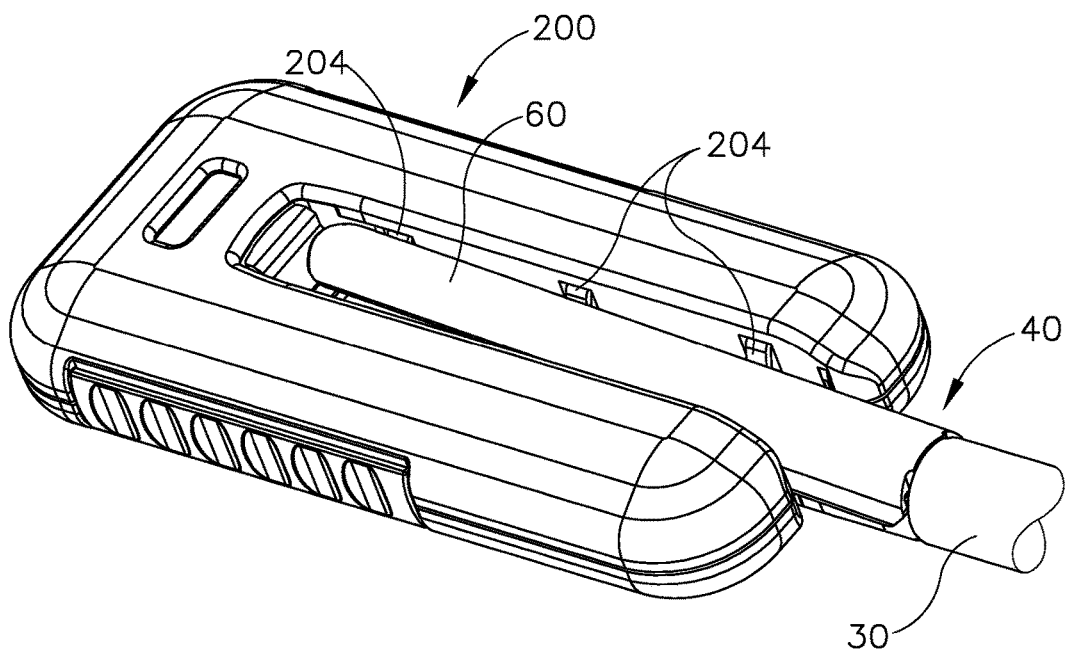
FIG. 16 depicts a perspective view of the end effector and the buttress assembly applicator of FIG. 15, with the buttress assembly applicator positioned in the end effector.

FIGS. 15 and 16 illustrate an exemplary end effector (40) configured to apply a buttress to a tissue site where a cutting and stapling operation is performed. End effector (40) includes distal end (141) and is connected with a shaft assembly (30). End effector (40) comprises an anvil (60), a lower jaw (50), and a staple cartridge (170) received by lower jaw (50). It will be appreciated that end effector (40) may be used in place of end effector (12) of instrument (10). End effector (40) may be integrally formed with instrument (10) or in the alternative may be interchangeable with end effector (12) of instrument (10).

FIGS. 15 and 16 also illustrate an exemplary buttress applicator (200). Buttress applicator (200) is configured to selectively retain buttress assemblies (100, 110). In the present example, buttress assembly (100) is selectively retained on a top side of applicator (200) and buttress assembly (110) is selectively retained on a bottom side of applicator (200). In some other versions, applicator (200) can be configured such that only one buttress assembly (100, 110) is selectively retained by buttress applicator (200).

Figure 2:
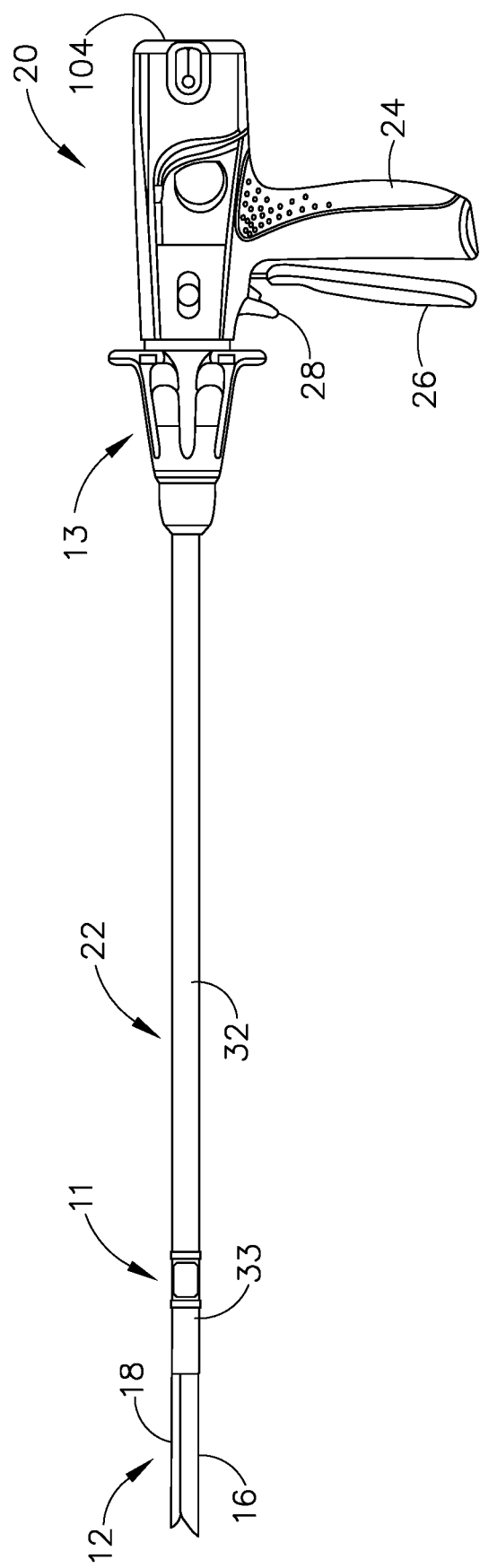
FIG. 2 depicts a side view of the instrument of FIG. 1.

To use buttress applicator (200) to load end effector (40) with buttress assemblies (100, 110), the operator would first position applicator (200) and end effector (40) such that end effector (40) is aligned with an open end (202) of applicator (200) as shown in FIG. 1. The operator would then advance end effector (40) distally (and/or retract applicator (200) proximally) to position buttress assemblies (100, 110) between anvil (60) and staple cartridge (170) as shown in FIG. 2. In order to load buttress assemblies (100, 110) on end effector (40), the operator may simply close end effector (40) by pivoting anvil (60) toward staple cartridge (170). Closure of end effector (40) results in the distal ends of anvil (60) and staple cartridge (170) bearing against retaining features (204) of buttress applicator (200) that are configured to selectively retain buttress assemblies (100, 110) with buttress applicator (200). This contact deflects such retaining features (204) of buttress applicator (200) to thereby permit contact between a surface of anvil (60) and buttress assembly (100) on one side of buttress applicator (200), and a surface of staple cartridge (170) and buttress assembly (110) on another side of buttress applicator (200). Buttress assemblies (100, 110) comprise an adhesive on their respective surfaces such that with end effector (40) clamping on both buttress assemblies (100, 110), buttress assemblies (100, 110) are adhered respectively to an underside of anvil (60) and a deck surface of staple cartridge (170). End effector (40) may then be re-opened (i.e., pivoting anvil (60) away from staple cartridge (170) and pulled away from buttress applicator (200). With retaining features (204) of applicator (200) disengaged from buttress assemblies (100, 110), end effector (40) may freely pull buttress assemblies (100, 110) away from buttress applicator (200) as end effector (40) is pulled away from buttress applicator (200). With buttress assemblies (100, 110) loaded on end effector (40), end effector (40) may then be used as described further below with reference to FIGS. 17A-18.

FIGS. 17A-17C show a sequence where an end effector (40) that has been loaded with buttress assemblies (100, 110) is actuated to drive staples (190) through two apposed layers of tissue ($T_1$, $T_2$), with buttress assemblies (100, 110) being secured to the same layers of tissue ($T_1$, $T_2$) by staples (190). In particular, FIG. 3A shows layers of tissue ($T_1$, $T_2$) positioned between anvil (60) and staple cartridge (170), with anvil (60) in the open position. As shown, anvil (60) comprises staple forming pockets (64). Buttress assembly (100) is adhered, via adhesive, to underside (65) of anvil (60); while buttress assembly (110) is adhered, via adhesive, to deck (73) of staple cartridge (170). Layers of tissue ($T_1$, $T_2$) are thus interposed between buttress assemblies (100, 110). Next, end effector (40) is closed, which drives anvil (60) to the closed position as shown in FIG. 17B. At this stage, layers of tissue ($T_1$, $T_2$) are compressed between anvil (60) and staple cartridge (170), with buttress assemblies (100, 110) engaging opposite surfaces of tissue layers ($T_1$, $T_2$). End effector (40) is then actuated, whereby a staple driver (75) drives staple (190) through buttress assemblies (100, 110) and tissue layers ($T_1$, $T_2$). As shown in FIG. 17C, crown (92) of driven staple (190) captures and retains buttress assembly (110) against layer of tissue ($T_2$). Deformed legs (94) of staple (190) capture and retain buttress assembly (100) against layer of tissue ($T_1$).

Figure 18:
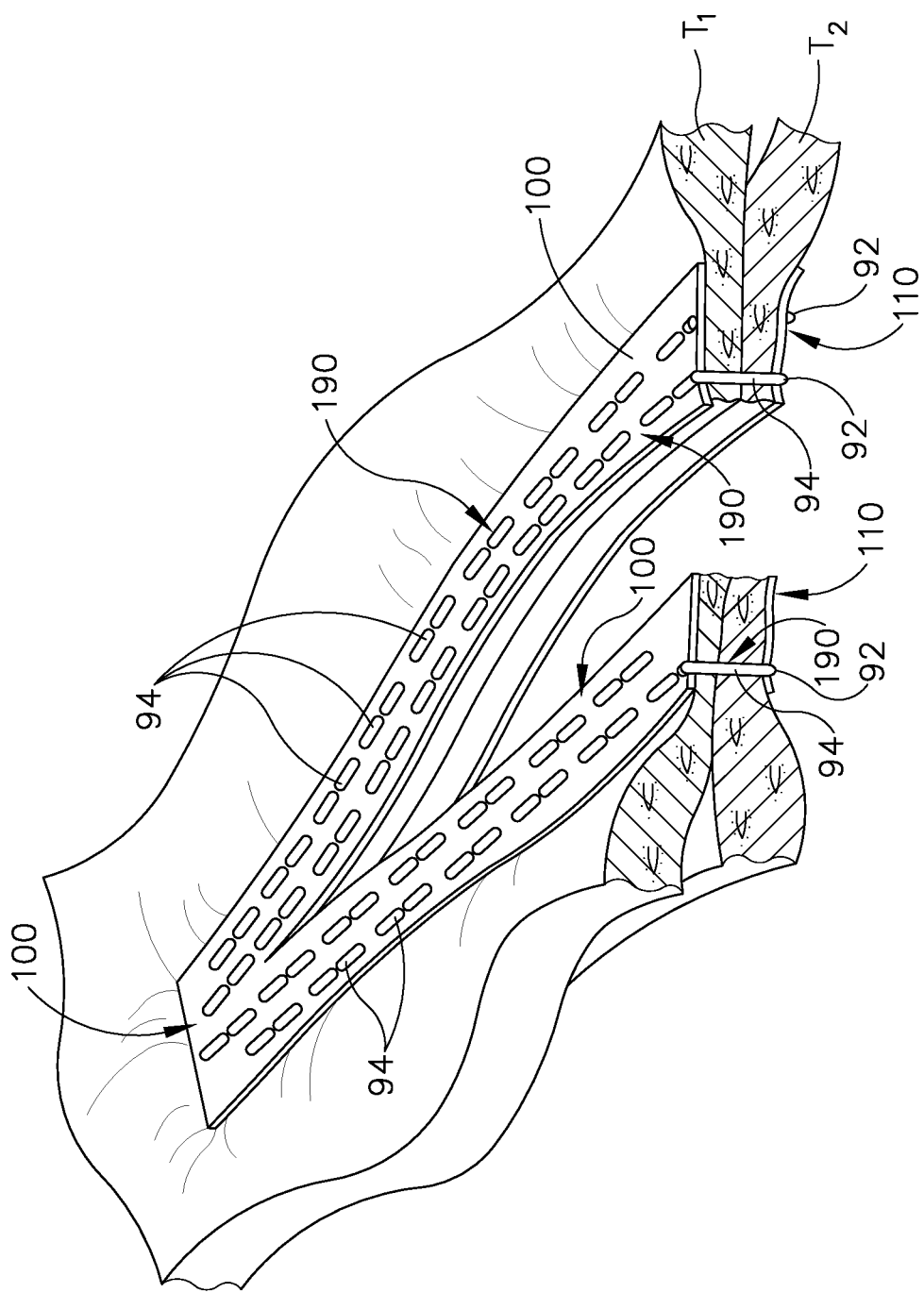
FIG. 18 depicts a perspective view of staples and the buttress assembly of FIG. 17A having been secured to the tissue by the end effector of FIG. 15.

It should be understood that a series of staples (190) will similarly capture and retain buttress assemblies (100, 110) against layers of tissue ($T_1$, $T_2$), thereby securing buttress assemblies (100, 110) to tissue ($T_1$, $T_2$) as shown in FIG. 18. As end effector (40) is pulled away from tissue (90) after deploying staples (190) and buttress assemblies (100, 110), buttress assemblies (100, 110) disengage end effector, such that buttress assemblies (100, 110) remain secured to tissue ($T_1$, $T_2$) with staples (190). Buttress assemblies (100, 110) thus provide structural reinforcement to the lines of staples (190). As can also be seen in FIG. 18, a knife member (not shown) passes through end effector (40) and in doing so also cuts through a centerline of buttress assemblies (100, 110), separating each buttress assembly (100, 110) into a corresponding pair of sections, such that each section remains secured to a respective severed region of tissue ($T_1$, $T_2$).

In the foregoing example, buttress assembly (100) is sized to span across the full width of underside (65) of anvil (60), such that a knife member (not shown) cuts through buttress assembly (100) during actuation of end effector (40). In some other examples, buttress assembly (100) is provided in two separate, laterally spaced apart portions, with one portion being disposed on underside (65) of anvil (60) on one half of anvil (60) and another portion being disposed on underside (65) of anvil (60) on the other half of anvil (60). In such versions, the knife member (not shown) does not cut through buttress assembly (100) during actuation of end effector (40).

Likewise, buttress assembly (110) may be sized to span across the full width of deck (73), such that the knife member (not shown) cuts through buttress assembly (110) during actuation of end effector (40). Alternatively, buttress assembly (110) may be provided in two separate, laterally spaced apart portions, with one portion being disposed on deck (73) on one half and another portion being disposed on deck (73) on the other half. In such versions, the knife member (not shown) does not cut through buttress assembly (110) during actuation of end effector (40).

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

VI. EXEMPLARY BUTTRESS APPLIER CARTRIDGE ASSEMBLY

Figure 19:
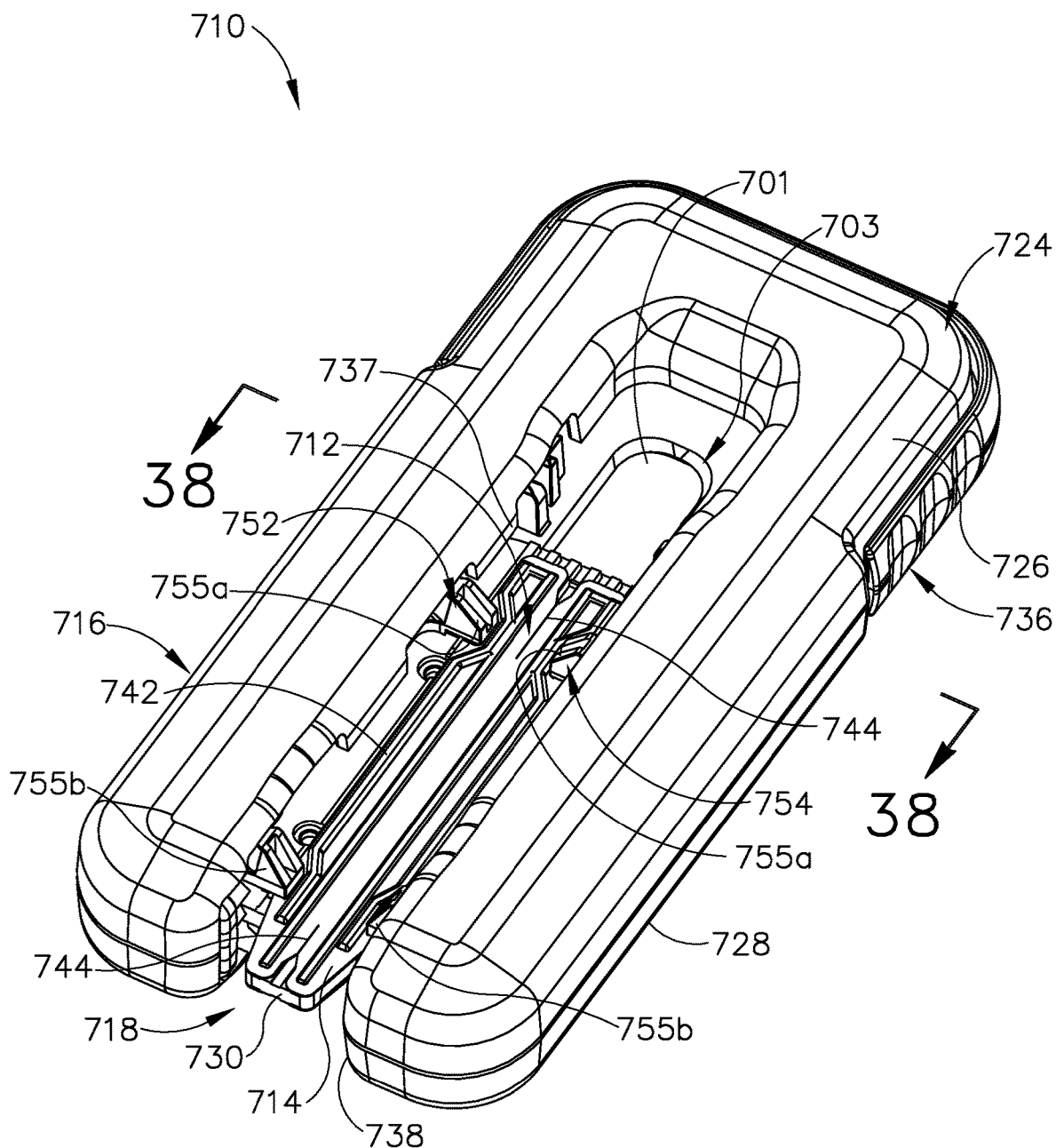
FIG. 19 depicts a perspective view of an exemplary buttress assembly applicator that includes an example of a buttress assembly applicator carrying an example of a buttress assembly for an upper jaw and an example of another buttress assembly for a lower jaw.

In some instances, it may be desirable to use an exemplary buttress applier cartridge assembly (710) as shown in FIG. 19 to equip a surgical instrument with a buttress assembly (712) for forming staples in tissue with a buttress (714). In some instances, buttress applier cartridge assembly (710)

may be referred to as a buttress assembly applicator (710). These terms as used herein should be understood to be interchangeable. Buttress (714) inhibits the formed staples from pulling through the tissue to thereby reduce a risk of tissue tearing at or near the site of formed staples. In addition to or as an alternative to providing structural support and integrity to a line of staples, buttress (714) may provide various other kinds of effects such as spacing or gap-filling, administration of therapeutic agents, and/or other effects. Prior to use with the surgical instrument, one or more buttress assemblies (712) is releasably retained on a buttress applier cartridge (716), which is configured to deposit one or more buttress assemblies (712) onto an end effector of a surgical instrument as discussed below.

FIG. 19 shows buttress applier cartridge assembly (710) including a pair of buttress assemblies (712) releasably retained on buttress applier cartridge (716), which supports and protects buttress assemblies (712) prior to use and further aids with loading buttress assemblies (712) on surgical instrument (10) (see FIG. 1). Buttress applier cartridge (716) of the present example includes an open end (718) and a closed end (720). Open end (718) is configured to receive an end effector such as any of those end effectors described herein, including but not limited to end effectors (12, 212, 312, 412, 512, 612). Buttress applier cartridge (716) further includes a housing assembly (724) having an upper housing (726) and a lower housing (728), which each generally define a "U" shape to present open end (718). Various components are interposed between upper and lower housings (726, 728). In particular, these components include a chassis (736) supporting a platform (730), which is also referred to as a compression layer (730).

Platform or compression layer (730) of the present example supports upper buttress assembly (712) on one side of platform (730) and lower buttress assembly (712) on the other side of platform (730). Platform (730) is exposed in recesses that are formed between the prongs of the "U" configuration of upper and lower housings (726, 728). Thus, upper housing (726) has an upper gap (737) extending to the open end (718) along an upper surface of platform (730), and lower housing (728) similarly has a lower gap (738) extending to the open end (718) along the lower surface of platform (730). The location of platform (730) and buttress assemblies (712) in such recesses may prevent inadvertent contact between buttress assemblies (712) and other devices in the operating room. In other words, upper and lower housings (726, 728) may provide some degree of physical shielding of buttress assemblies (712) while buttress assemblies are retained on platform (730).

Additional features may be combined as applicable with the following example of buttress applier cartridge assembly (710). Such features are described in U.S. Pat. App. No. 16/235,473, entitled "Adhesive Distribution on Buttress for Surgical Stapler," filed on Dec. 28, 2018, published as U.S. Pub. No. 2020/0205820 on Jul. 2, 2020; U.S. Pat. No. 16/235,488, entitled "Configuration of Buttress for Surgical Stapler," filed on Dec. 28, 2018, published as U.S. Pub. No. 2020/0205821 on Jul. 2, 2020; U.S. Pat. App. No. 16/235,503, entitled "Surgical Stapler Buttress with Tissue In-Growth Promotion," filed on Dec. 28, 2018, published as U.S. Pub. No. 2020/0205822 on Jul. 2, 2020; U.S. Pat. No. 16/235,541, entitled "Packaging for Surgical Stapler Buttress," filed on Dec. 28, 2018, published as U.S. Pub. No. 2020/0205824 on Jul. 2, 2020; U.S. Pat. No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020; U.S. Pat. No. 16/235,630, entitled "Curved Tip Surgical Stapler Buttress Assembly Applicator with Opening Feature for Curved Tip Alignment," filed on Dec. 28, 2018, published as U.S. Pub. No. 2020/0205826 on Jul. 2, 2020; U.S. Pat. No. 16/235,617, entitled "Method of Applying Buttresses to Surgically Cut and Stapled Sites," filed on Dec. 28, 2018, published as U.S. Pub. No. 2020/0205825 on Jul. 2, 2020; U.S. Pat. No. 29/675,168, entitled "Applicator for Surgical Stapler Buttress," filed on Dec. 28, 2018; U.S. Pat. No. 29/675,170, entitled "Buttress for Surgical Stapler," filed on Dec. 28, 2018; U.S. Pat. No. 29/675,172, entitled "Tray for Surgical Stapler Buttress Applicator," filed on Dec. 28, 2018; U.S. Pat. App. No. 29/675,197, entitled "Applicator for a Surgical Stapler Buttress," filed on Dec. 28, 2018; and U.S. Pat. No. 29/675,199entitled "Buttress Assembly for a Surgical Stapler," filed on even date herewith Dec. 28, 2018, the disclosures of which are hereby incorporated by reference.

A. Exemplary Buttress Assembly

With respect to FIG. 19, upper and lower buttress assemblies (712) are structurally identical, but for the relative positions of upper and lower buttress assemblies (712) retained on buttress applier cartridge (716). Buttress applier cartridge assembly (710) may thus be used in more than one orientation with surgical instrument (10) and its respective end effectors that may be combined therewith. It will be appreciated that the following description of upper buttress assembly (712) similarly applies to lower buttress assembly (712) but for the respective orientations.

Upper buttress assembly (712) includes buttress (714) and an upper adhesive layer (742). Buttress (714) of the present example more particularly has a three-layer, polymer construction including a core layer sandwiched between two outer layers to be collectively strong yet flexible to support a line of staples. In the present example, core layer is a polyglactin 910 material, which is manufactured and sold by Ethicon, Inc. of Somerville, N.J. as VICRYL, whereas each outer layer is a polydioxanone (PDO) film material. Buttress (714) of the present example is formed by laminating core layer between outer layers under a predetermined pressure, a predetermined temperature, and a predetermine time. Buttress (714) is further mechanically cut to size thereby inhibiting abrasive edges, such as burrs and/or delamination, that could damage sensitive tissues. It will be appreciated that alternative methods of cutting buttresses (714), such as a laser cutting or hot knife cutting, may be similarly used.

By way of further example only, each buttress (714) may comprise one or more of the following: NEOVEIL absorbable PGA felt by Gunze Limited, of Kyoto, Japan; SEAM-GUARD polyglycolic acid: trimethylene carbonate (PGA: TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress (714) will be apparent to those of ordinary skill in the art in view of the teachings herein.

In addition or in the alternative, each buttress (714) may comprise a material including, for example, a hemostatic agent such as fibrin to assist in coagulating blood and reduce bleeding at the severed and/or stapled surgical site along tissue. As another merely illustrative example, each buttress (714) may comprise other adjuncts or hemostatic agents such as thrombin may be used such that each buttress (714)

may assist to coagulate blood and reduce the amount of bleeding at the surgical site. Other adjuncts or reagents that may be incorporated into each buttress (714) may further include but are not limited to medical fluid or matrix components. Merely illustrative examples of materials that may be used to form each buttress (714), as well as materials that may be otherwise incorporated into each buttress (714), are disclosed in U.S. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used.

By way of further example only, each buttress (714) may be constructed in accordance with at least some of the teachings of U.S. Pat. No. 10,123,798, entitled "Tissue Thickness Compensator Comprising Controlled Release and Expansion," issued Nov. 13, 2018, the disclosure of which is incorporated by reference herein; U.S. Pat. Pub. No. 2013/0068816, entitled "Surgical Instrument and Buttress Material," published Mar. 21, 2013, now abandoned, the disclosure of which is incorporated by reference herein; U.S. Pat. No. 9,999,408, entitled "Surgical Instrument with Fluid Fillable Buttress," issued Jun. 19, 2018, the disclosure of which is incorporated by reference herein; U.S. Pat. No. 8,814,025, entitled "Fibrin Pad Matrix with Suspended Heat Activated Beads of Adhesive," issued Aug. 26, 2014, the disclosure of which is incorporated by reference herein; U.S. Pat. No. 8,899,464, entitled "Attachment of Surgical Staple Buttress to Cartridge," issued Dec. 2, 2014, the disclosure of which is incorporated by reference herein; U.S. Pat. No. 9,492,170, entitled "Device for Applying Adjunct in Endoscopic Procedure," issued Nov. 15, 2016, the disclosure of which is incorporated by reference herein; U.S. Pat. No. 8,998,060, entitled "Resistive Heated Surgical Staple Cartridge with Phase Change Sealant," issued Apr. 7, 2015, the disclosure of which is incorporated by reference herein; U.S. Pat. No. 9,393,018, entitled "Surgical Staple Assembly with Hemostatic Feature," issued Jul. 19, 2016, the disclosure of which is incorporated by reference herein; U.S. Pat. No. 9,101,359, entitled "Surgical Staple Cartridge with Self-Dispensing Staple Buttress," issued Aug. 11, 2015, the disclosure of which is incorporated by reference herein; U.S. Pat. No. 9,198,644, entitled "Anvil Cartridge for Surgical Fastening Device," issued Dec. 1, 2015, the disclosure of which is incorporated by reference herein; U.S. Pat. Pub. No. 2013/0075447, entitled "Adjunct Therapy for Applying Hemostatic Agent," published Mar. 28, 2013, now abandoned, the disclosure of which is incorporated by reference herein; U.S. Pat. No. 9,211,120, entitled "Tissue Thickness Compensator Comprising a Plurality of Medicaments," issued Dec. 15, 2015, the disclosure of which is incorporated by reference herein; U.S. Pat. Pub. No. 2015/0351758, entitled "Adjunct Materials and Methods of Using Same in Surgical Methods for Tissue Sealing," published Dec. 10, 2015, issued as U.S. Pat. No. 10,172,611 on Jan. 8, 2019, the disclosure of which is incorporated by reference herein; U.S. Pat. Pub. No. 2017/0049444, entitled "Implantable Layers for a Surgical Instrument," published Feb. 23, 2017, the disclosure of which is incorporated by reference herein; U.S. Pat. Pub. No. 2017/0055986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10, 433,846 on Oct. 8, 2019, the disclosure of which is incorporated by reference herein; and/or U.S. Pat. Pub. No. 2017/0086842, entitled "Method for Applying an Implantable Layer to a Fastener Cartridge," published Mar. 30, 2017, the disclosure of which is incorporated by reference herein.

Furthermore, buttress (714) is configured to be cut by a knife (not shown) from a proximal portion of buttress (714), along an intermediate portion of buttress (714), and further through a distal portion of buttress (714) such that inward edges are adjacent to cut tissue. Buttress (714) further includes a longitudinally extending pre-cut slit (744) configured to receive knife (not shown) and aid in separating lateral portions of buttress (714) as inward edges form therealong.

Upper adhesive layer (742) is provided on outer layer of buttress (714) in order to adhere buttress (714) within end effectors described herein. Adherence of the buttress (714) can occur through a variety of mechanisms including but not limited to a pressure sensitive adhesive. In the case of pressure sensitive adhesion, adhesion occurs upon the application of at least a predetermined minimum force. In some versions, each adhesive layer (742) includes a pressure sensitive adhesive material. Examples of various suitable materials that may be used to form adhesive layers (742) are disclosed in U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019 the disclosure of which is incorporated by reference herein. Alternatively, any other suitable materials may be used. As shown in the present example, adhesive layer (742) is applied to form a continuous outer seal to enhance longevity once applied to an end effector.

It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (742) will be apparent to those of ordinary skill in the art in view of the teachings herein.

B. Exemplary Buttress Applier Cartridge

Figure 20:
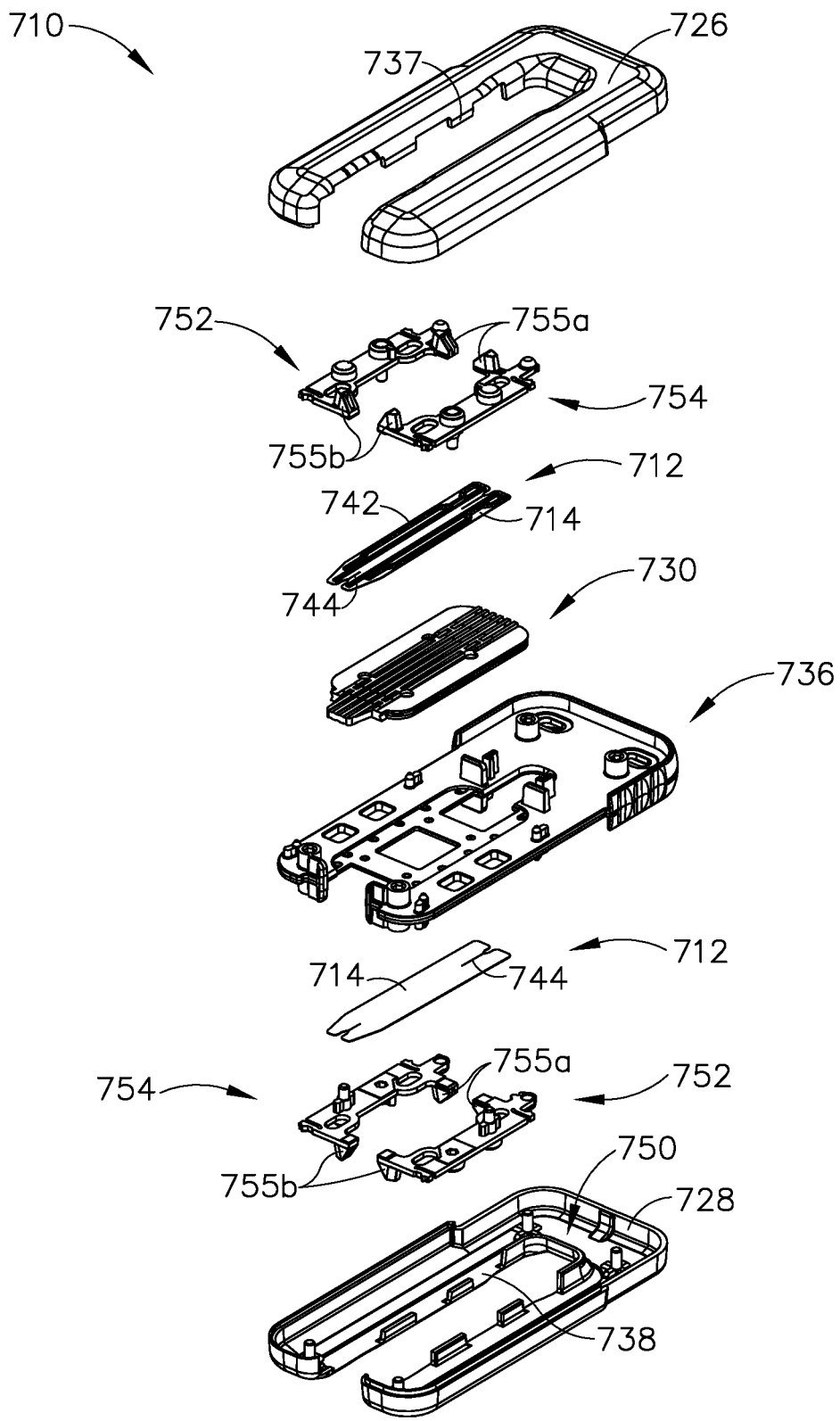
FIG. 20 depicts an exploded perspective view of the buttress assembly applicator of FIG. 19 including a chassis and a platform in addition to a pair of buttress assemblies.

As shown in FIG. 20, buttress applier cartridge (716) includes chassis (736) supporting platform (730) as well as upper and lower housings (726, 728) of housing assembly (724) configured to connect together to define an interior space (750). An upper left actuator sled (752) and an upper right actuator sled (754) are movably connected to an upper face chassis (736) within interior space (750), while a lower left actuator sled (752) and a lower right actuator sled (754) are movably connected to a lower face of chassis (736) within interior space (750). Upper right and left actuator sleds (752, 754) retain upper buttress assembly (712) on platform (730) in a restraint position, but are configured to move from the restraint position to a release position for depositing the upper buttress assembly (712) on an end effector, such as any of the end effectors described herein. Similarly, lower right and left actuator sleds (752, 754) retain lower buttress assembly (712) on platform (730) in the restraint position, but are configured to move from the restraint position to the release position for depositing the lower buttress assembly (712) on an end effector, such as any of the end effectors described herein. In the present example, left actuator sled (752) is distinct from right actuator sled (754) for reasons discussed below in greater detail. Also, upper and lower right actuator sleds (752) are structurally identical to each other, and upper and lower left actuator sleds (754) are structurally identical to each other. Thus, upper and lower actuator sleds (752, 754) are interchangeable in this respect and any discussion contained herein directed to a pair of upper actuator sleds (752, 754) is similarly applicable to a pair of lower actuator sleds (752, 754).

Each actuator sled (752, 754) includes a pair of arms (755a, 755b) extending laterally inward to selectively and releasably secure buttress assemblies (712) to platform (730). Arms (755a, 755b) may also be referred to as retaining features or retention members, similar to the retaining features (204) described above with respect to applicator (200) in FIGS. 15 and 16. In particular, FIG. 20 show arms (755a, 755b) positioned such that buttress assemblies (712) are interposed between the free ends of arms (755a, 755b) and platform (730). Arms (755a, 755b) are movable laterally outwardly such that arms (755a, 755b) disengage buttress assemblies (712), thereby enabling buttress assemblies (712) to be removed from platform (730). In the present example, arms (755a, 755b) are configured to bear against buttress assemblies (712) in the restraint position, thereby pinching buttress assemblies (712) against platform (730). Other suitable ways in which arms (755a, 755b) may engage buttress assemblies (712) will be apparent to those of ordinary skill in the art in view of the teachings herein.

Chassis (736) is configured to cooperate with upper and lower housings (726, 728) to provide a mechanical ground for moving components of buttress applier cartridge (716) and provide structural support for components of buttress applier cartridge (716). Chassis (736) further includes integral gripping features (756) that are exposed on opposite sides of housing assembly (724). Gripping features (756) have a surface geometry configured to promote an operator's grip of buttress applier cartridge (716) during use of buttress applier cartridge (716). Various suitable configurations that may be used for gripping features (756) will be apparent to those of ordinary skill in the art in view of the teachings herein. Similarly, various surface treatments (e.g., elastomeric material, etc.) that may be applied to gripping features (756) will be apparent to those of ordinary skill in the art in view of the teachings herein.

Figure 21:
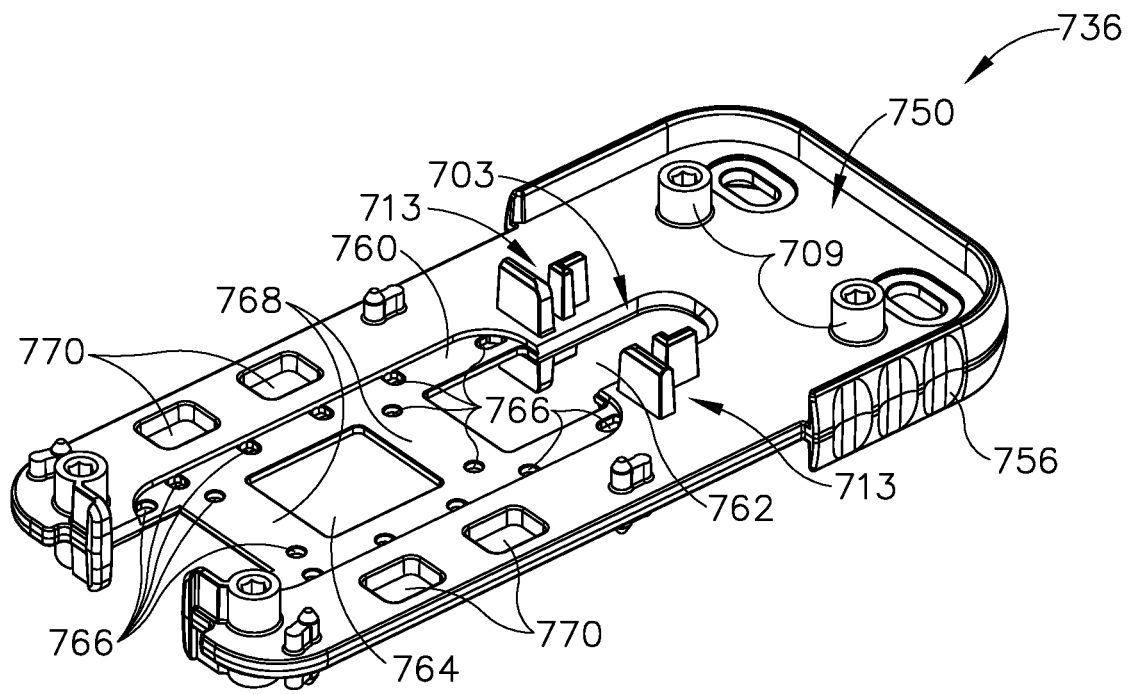
FIG. 21 depicts a front perspective view of the chassis of FIG. 20.

With respect to FIG. 21, platform (730) is connected to and supported by chassis (736) to secure platform (730) relative to upper and lower housing (726, 728). In the present example, platform (730) is unitarily formed and molded to a rigid web portion (758) including a frame (760) and defining a plurality of holes (762, 764, 766) configured provide material overlap for mold securement. Holes (762, 764, 766) more particularly include an upper slot (762) and central slot (764) that extend through frame (760) as well as a plurality of through holes (766) spaced laterally about slot (762, 764). Frame (760) also extends laterally across central slot (764) at bridge portions (768) to provide additional structural rigidity to chassis (736) while providing platform (730) with sufficient clearance for resilient deformation as discussed below in greater detail. Thereby, slots (762, 764) and through holes (766) receive a resilient, elastomeric material to form and secure the material as platform (730) to chassis (736). While the present platform (730) is molded to chassis (736), it will be appreciated that platform (730) may be alternatively secured to chassis (736), and thus the attachment of platform (730) to chassis (736) is not intended to be limited to the particular rigid web portion (758) and molding as discussed herein. Various suitable materials and structural configurations that may be used to form platform (730) will be apparent to those of ordinary skill in the art in view of the teachings herein.

Chassis (736) further includes a plurality of sled clearance holes (770) arranged in a pair of rows on opposing lateral sides of chassis (736). Left and right actuator sleds (752, 754) connect together on opposing sides of chassis (736) through such sled clearance holes (770) to slide inwardly together in connected pairs. Additional details regarding connection and actuation of left and right actuator sleds (752, 754) will be discussed below in greater detail. However, it will be appreciated that any such hole through chassis (736) to provide for fastening clearance of left and right actuator sleds (752, 754) may be used, and the invention is not intended to be unnecessarily limited to sled clearance holes (70) as discussed herein.

i. Exemplary Varying Stiffness Platform for Supporting Buttress Assemblies

Figure 22:
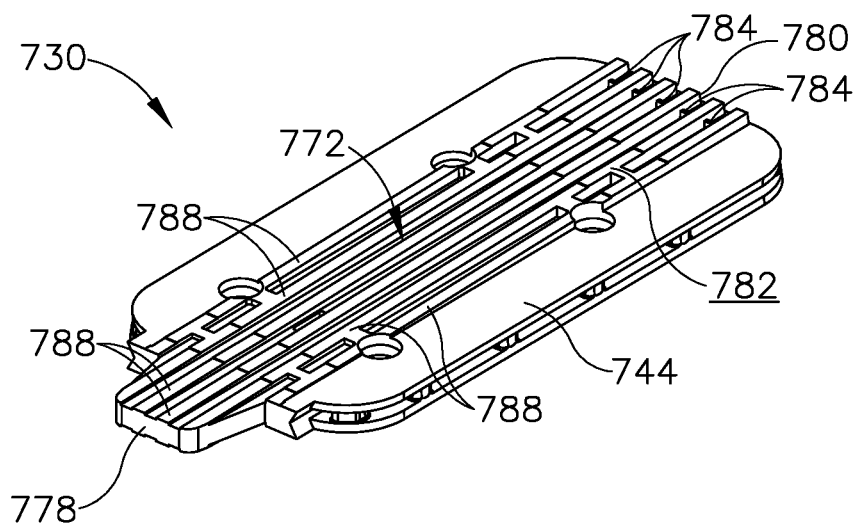
FIG. 22 depicts a front perspective view of the platform of FIG. 20.
Figure 23:
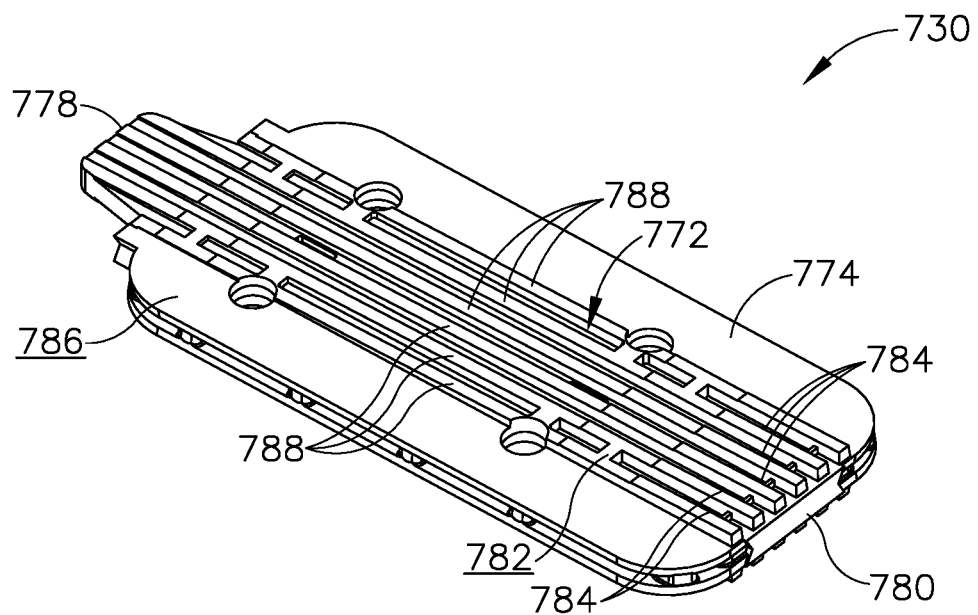
FIG. 23 depicts a rear perspective view of the platform of FIG. 20.
Figure 24:
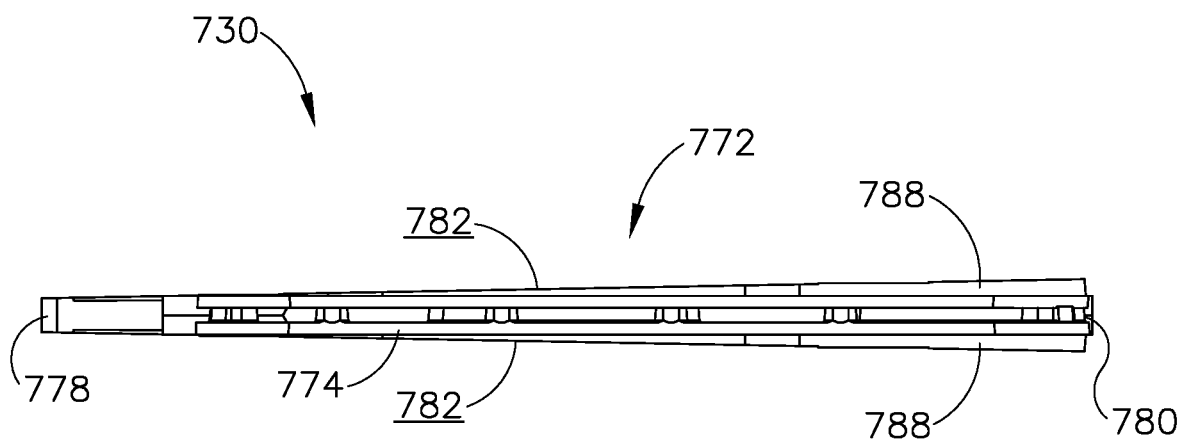
FIG. 24 depicts an elevational side view of the platform of FIG. 20.

FIGS. 22-24 show one example of platform (730) in additional detail as including a pad (772) and perimeter region (774) laterally extending therefrom. Perimeter region (774) is positioned in within frame (760) and extends into through holes (766) to secure pad (772) to chassis (736). In some versions, platform (730) is formed of a material that provides a high coefficient of friction, thereby reducing any tendency that buttress assemblies (712) might otherwise have to slide along corresponding surfaces of platform (730). For instance, platform (730) may comprise a resilient, elastomeric material, such as silicone, to be molded to be formed as securement (774) and pad (772). One example silicone material is a 30 Durometer, Shore A silicone. To this end, pad (772) is formed with varying stiffness along its longitudinal length to simultaneously provide sufficient reactionary forces of at least the predetermined minimum force for adhesion while accommodating a parallel-camber orientation, an over-camber orientation, and an under-camber orientation of an end effector as discussed below in greater detail. As used herein, the term "parallel-camber orientation" refers to an upper jaw and a lower jaw of an end effector being functionally parallel to each other. The term "over-camber orientation" refers to an upper jaw of an end effector being over rotated relative a lower jaw of an end effector. The term "under-camber orientation" refers to an upper jaw being under rotated relative to a lower jaw of an end effector.

With respect to FIGS. 22 and 23, a resilient proximal end (778) of pad (772) has a proximal end stiffness and a proximal transverse depth, whereas a resilient distal end (780) of pad (772) has a distal end stiffness and a distal transverse depth. In the present example, proximal end stiffness is generally greater than the distal end stiffness such that initial compression of distal end (780) requires less compressive force than compression of proximal end (778). Of course, further compression of distal end (780) relative to proximal end (778) may result in distal end stiffness increasing to or even exceeding proximal end stiffness so long as the lesser stiffness of distal end (780) is included therein for accommodating the over-cambered orientation of an end effector.

In addition, distal transverse depth is greater than proximal transverse depth. Thereby, the greater distal transverse depth effectively props up buttress assembly (712) for improved engagement with an end effector in the under-camber orientation, but the decreased distal end stiffness allows for greater compression to accommodate an end effector in the over-camber orientation. Pad (772) of the present example is wedge-shaped having opposing ramp surfaces (782) continuously tapering together from the distal end (780) to the proximal end (778) for accommodating parallel-camber, over-camber, and under-camber orientations along the entire longitudinal length of pad (772). In some examples, depths and stiffnesses along pad (772) are configured to receive a full range of over-camber to under-camber orientations based on determined manufacturing tolerances of an end effector.

Pad (772) shown in FIGS. 22-24 is unitarily formed of a resilient material having a consistent stiffness throughout. Such longitudinally varying stiffness discussed above is thus generated by forming a plurality of reliefs, such as channels (784), in at least the distal end (780) to reduce the distal end stiffness relative to the proximal end stiffness. In the present example, channels (784), such as five channels (784) are equally spaced laterally apart from each other and longitudinally extend from distal end (780) to proximal end (778). Channels (784) further define varying channel depths in the longitudinal direction along pad (772). More particularly, upper channels (784) extend transversely downward from upper ramp surface (782) to upper base surface (786), whereas lower channels (784) extend transversely upward from lower ramp surface (782) to lower base surface (786). In turn, a plurality of ribs (788) are defined between channels (784) and similarly extend from ramp surfaces (782) to base surfaces (786) to support buttress assemblies (712) and have varying stiffness from the proximal end (778) to the distal end (780) on each opposing side of pad (772).

ii. Exemplary Restraint Features for Retention of Buttress Assemblies on Varying Stiffness Platform FIGS. 20 and 25-28 show restraint features, such as left and right actuator sleds (752, 754) discussed briefly above for releasably securing buttress assemblies (712) to platform (730) in the restraint position. Each of left and right actuator sleds (752, 754) has arms (755a, 755b) configured to accommodate varying transverse depths along the longitudinal length of pad (772). More particularly, arms (755a, 755b) include a distal arm (755a) and a proximal arm (755b) spaced longitudinally apart from each other and extending laterally inward toward platform (730). Each distal arm (755a) and proximal arm (755b) of left or right actuator sled (752, 754) transversely extends toward platform (730) such that each of distal arm (755a) and proximal arm (755b) is offset from the other arms (755a, 755b) in the transverse direction. Thereby, distal arm (755a) and proximal arm (755b) are transversely spaced from the ramp surface (782) to trace the contour of the ramp surface (782).

Figure 25:
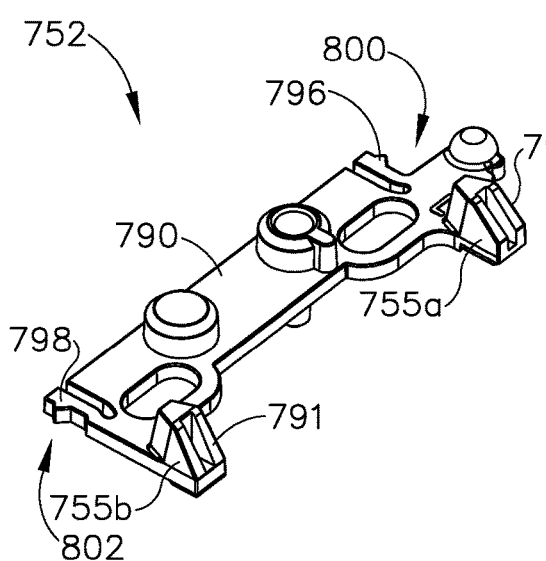
FIG. 25 depicts a top perspective view of a left actuator sled of the buttress assembly applicator of FIG. 20.
Figure 26:
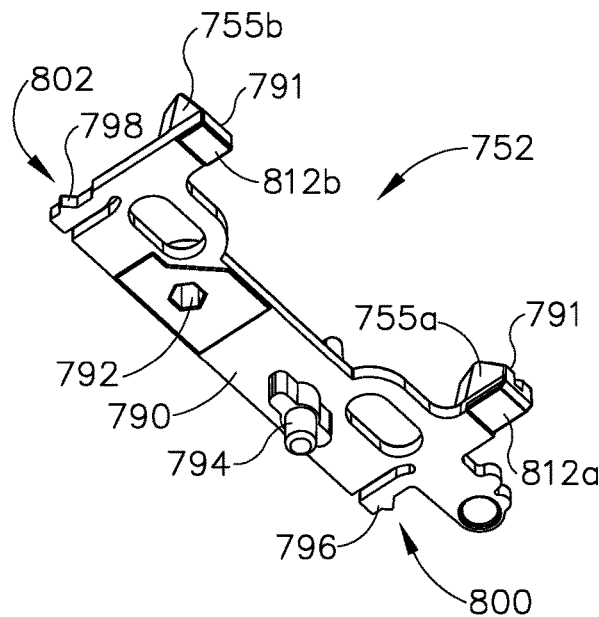
FIG. 26 depicts a bottom perspective view of the left actuator sled of FIG. 25.

With respect to FIGS. 25 and 26, upper left actuator sled (752) has a longitudinally extending upper left sled body (790) with distal and proximal arms (755a, 755b) laterally extending inward toward the right. Each arm (755a, 755b) of left actuator sled (752) has a cam surface (791) configured to receive an end effector thereagainst to urge left actuator sled (752) toward the release position. In addition, a dowel hole (792) opens downward and is respectively positioned on a portion of upper left sled body (790). A dowel (794) extends downward from left sled body (790) and in longitudinal alignment with outer dowel hole (792). In order to arrest movement of upper left actuator sled (752) in the restraint and release positions, a distal cantilever catch (796) laterally extends to the left from the distal portion of upper left sled body (790), and a proximal cantilever catch (798) laterally extends to the left from the proximal portion of upper left sled body (790). Distal and proximal cantilever catches (796, 798) are respectively portions of distal and proximal detent couplings (800, 802) discussed below in greater detail.

Figure 27:
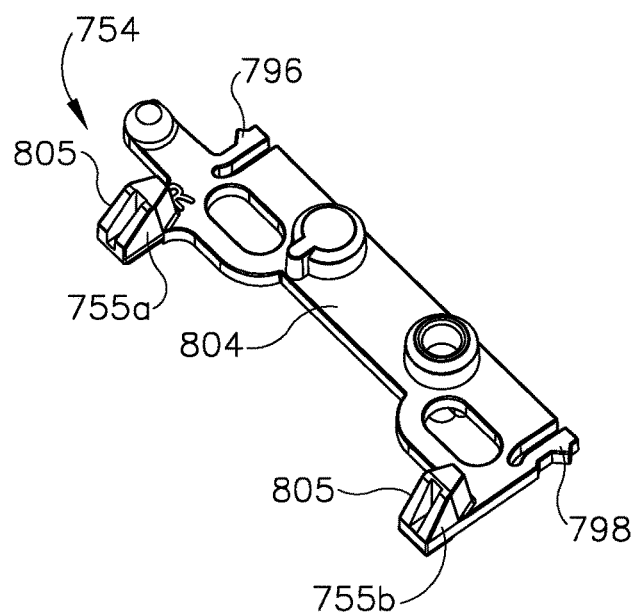
FIG. 27 depicts a top perspective view of a right actuator sled of the buttress assembly applicator of FIG. 20.
Figure 28:
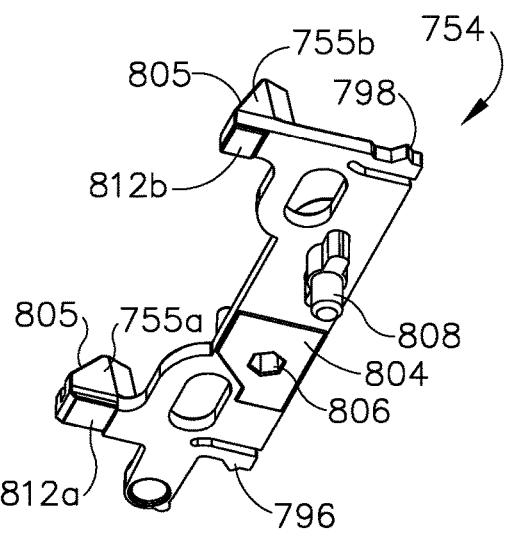
FIG. 28 depicts a bottom perspective view of the right actuator sled of FIG. 27.

With respect to FIGS. 27 and 28, upper right actuator sled (754) has a longitudinally extending upper right sled body (804) with distal and proximal arms (755a, 755b) laterally extending inward toward the left. Each arm (755a, 755b) of right actuator sled (754) has a cam surface (805) configured to receive an end effector thereagainst to urge left actuator sled (752) toward the release position. In addition, a dowel hole (806) opens downward and is positioned on upper right sled body (804). A dowel (808) extends downward from right sled body (804) and is positioned in longitudinal alignment with inner dowel hole (806). In order to arrest movement of upper right actuator sled (754) in the restraint and release positions, another distal cantilever catch (796) laterally extends to the right from the distal portion of upper right sled body (804), and another proximal cantilever catch (796) laterally extends to the right from the proximal portion of upper right sled body (804). Again, distal and proximal cantilever catches (796, 798) are respectively portions of distal and proximal detent couplings (800, 802) discussed below in greater detail.

Figure 29:
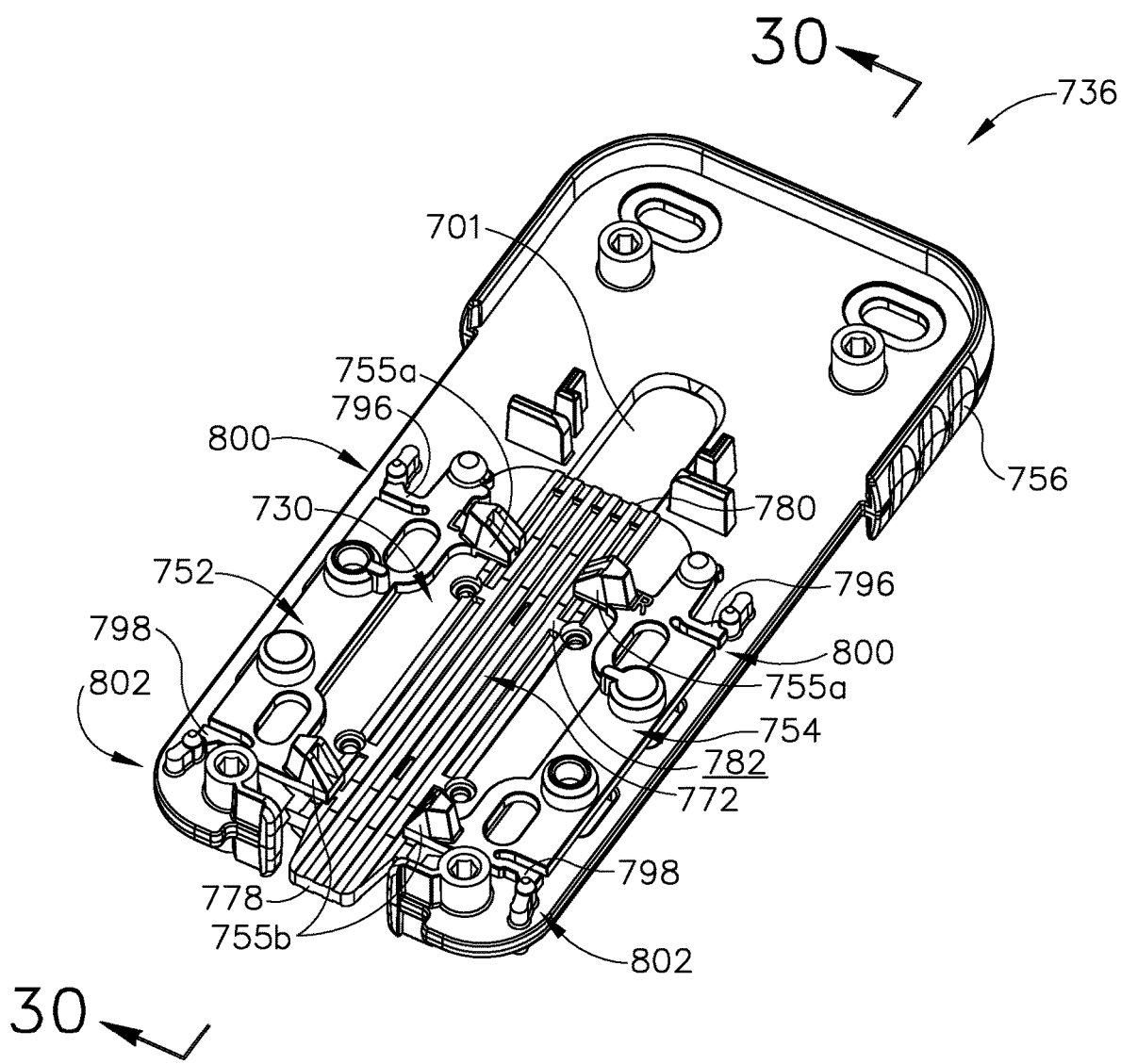
FIG. 29 depicts a perspective view of the chassis and the platform of FIG. 21 and FIG. 22 with pairs of left and right actuator sleds of FIG. 25 and FIG. 27.
Figure 30:
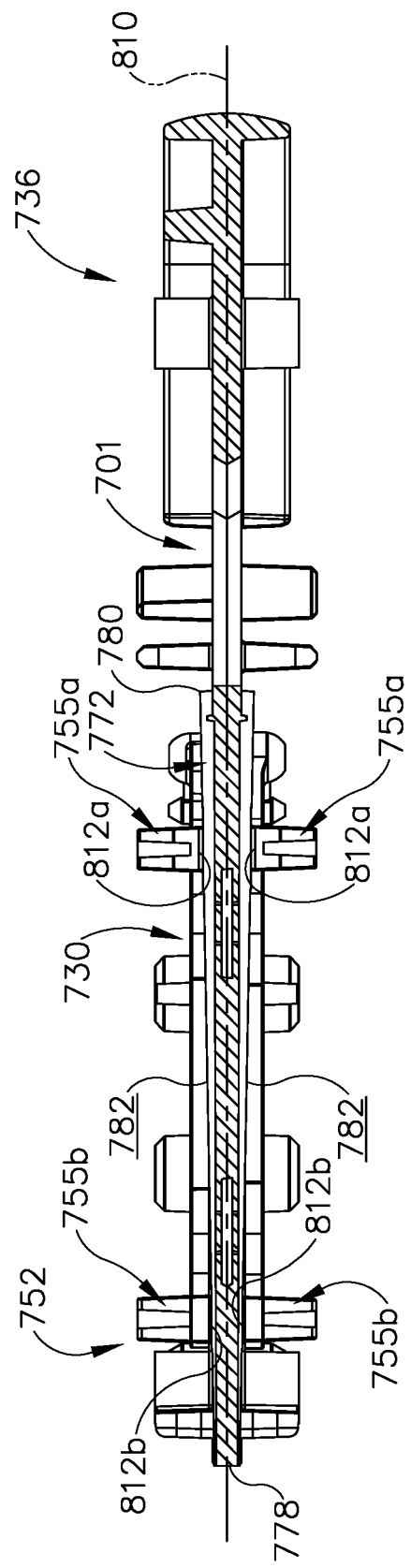
FIG. 30 depicts a cross-sectional view of the chassis, the platform, and the actuator sleds of FIG. 29 taken along section line 30-30 of FIG. 29.

FIG. 20 and FIGS. 29 and 30 show upper right and left actuator sleds (752, 754) as discussed above in detail as well as lower right and left actuator sleds (752, 754). As briefly discussed above, the description of upper right and left actuator sleds (752, 754) similarly applies to lower right and left actuator sleds (752, 754) with like features having like numbers, but with reversed transverse directions (e.g. lower, upward, etc.). To this end, upper left actuator sled (752) and lower right actuator sled (754) connect together as outer dowel (808) snaps into outer dowel hole (792) and inner dowel (794) snaps into inner dowel hole (806) with chassis (736) positioned therebetween. Upper right actuator sled (754) and lower left actuator sled (752) similarly connect together as outer dowel (808) snaps into outer dowel hole (792) and inner dowel (794) snaps into inner dowel hole (806) with chassis (736) positioned therebetween. Each of inner and outer dowels (794, 808) extend through sled clearance holes (770) to slidably connect left and right actuator sleds (752, 754) to chassis (736).

FIG. 30 shows one example of a pair of distal arms (755a) and a pair of proximal arms (755b) respectively having platform (730) positioned therebetween and tracing opposing ramp surfaces (782). A central plane (810) is shown in FIG. 12 bisecting upper and lower portions of buttress applier cartridge (716) through a central core of platform (730). Distal arm (755a) has a distal retention surface (812a) transversely offset from central plane (810) a relatively greater distance, and proximal arm (755b) has a proximal retention surface (812b) transversely offset from central plane (810) a relatively lesser distance. Thereby, greater and lesser distances of distal and proximal retention surfaces (812a, 812b) trace ramp surfaces (782) tapering from distal end (780) of pad (772) to proximal end (778) of pad (772). Thus, distal and proximal retention surfaces (812a, 812b) are offset in the transverse direction from each other and from central plane (810). In the present example, each of distal arm (755a) and proximal arm (755b) are transversely spaced from the ramp surface (782) an equal transverse dimension such that arms (755a, 755b) equally trace ramp surfaces (782) tapering from distal end (780) of pad (772) to proximal end (778) of pad (772).

Figure 31:
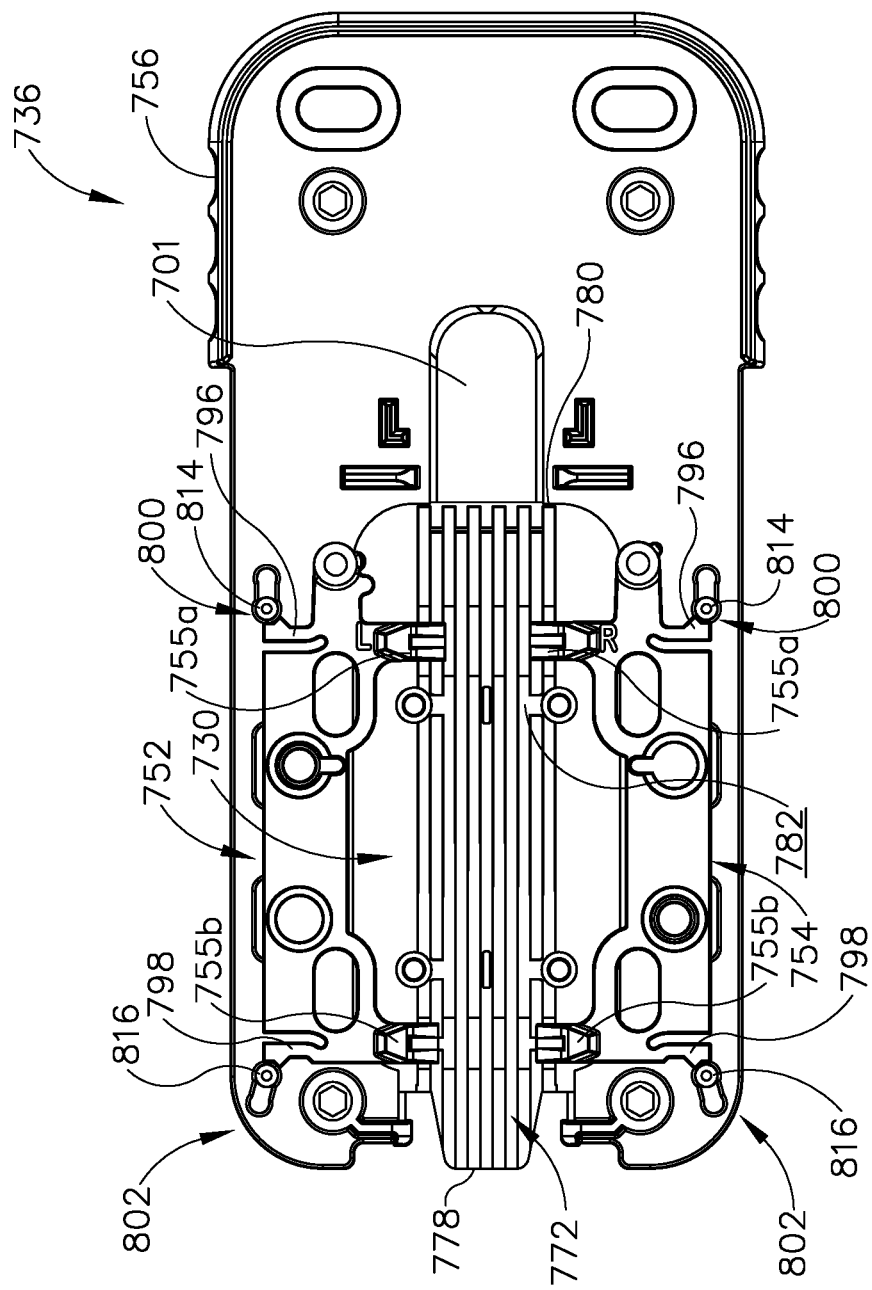
FIG. 31 depicts a top view of the chassis, the platform, and the actuator sleds of FIG. 29 in a restraint position.
Figure 32:
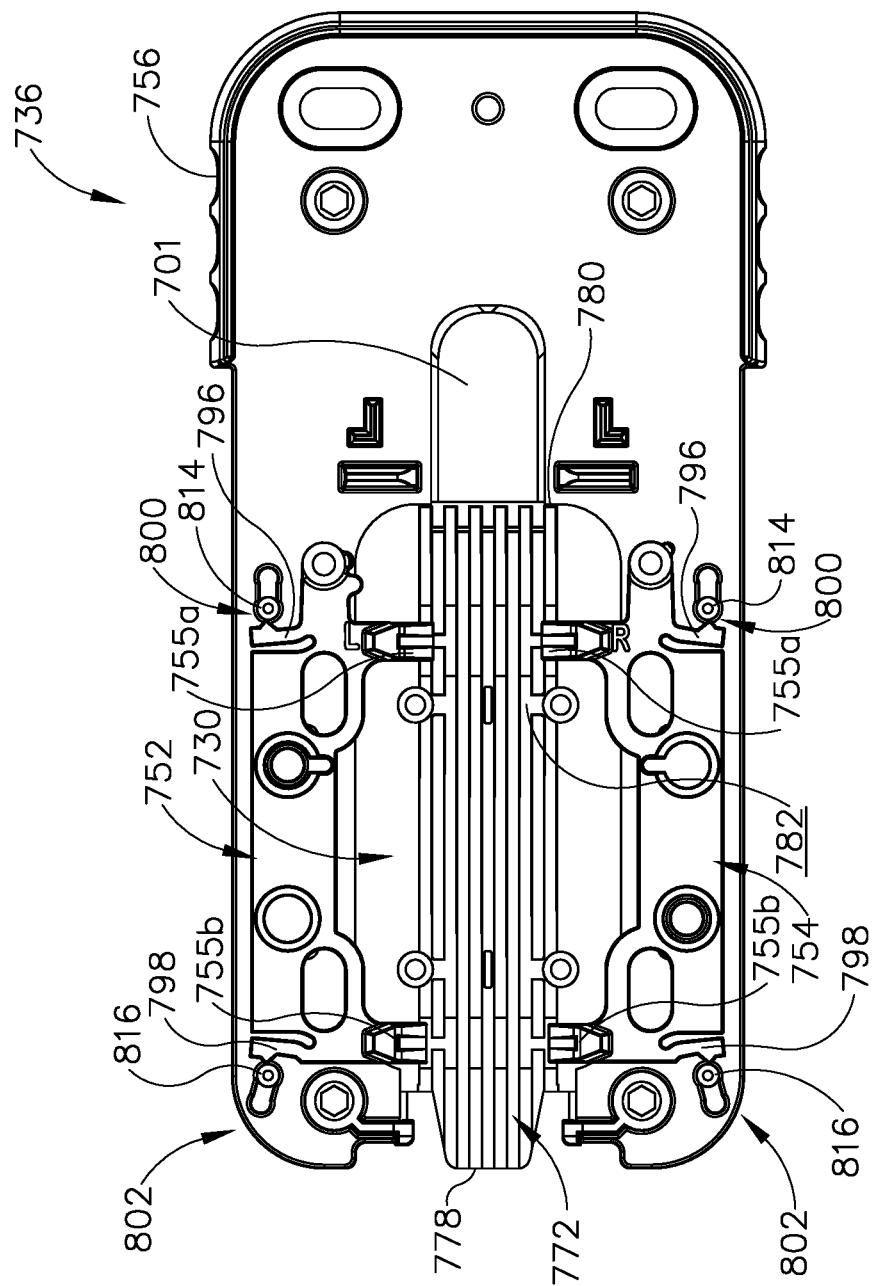
FIG. 32 depicts the top view of the chassis, the platform, and the actuator sleds similar to FIG. 31, but showing the actuator sleds being directed from the restraint position toward a release position.
Figure 33:
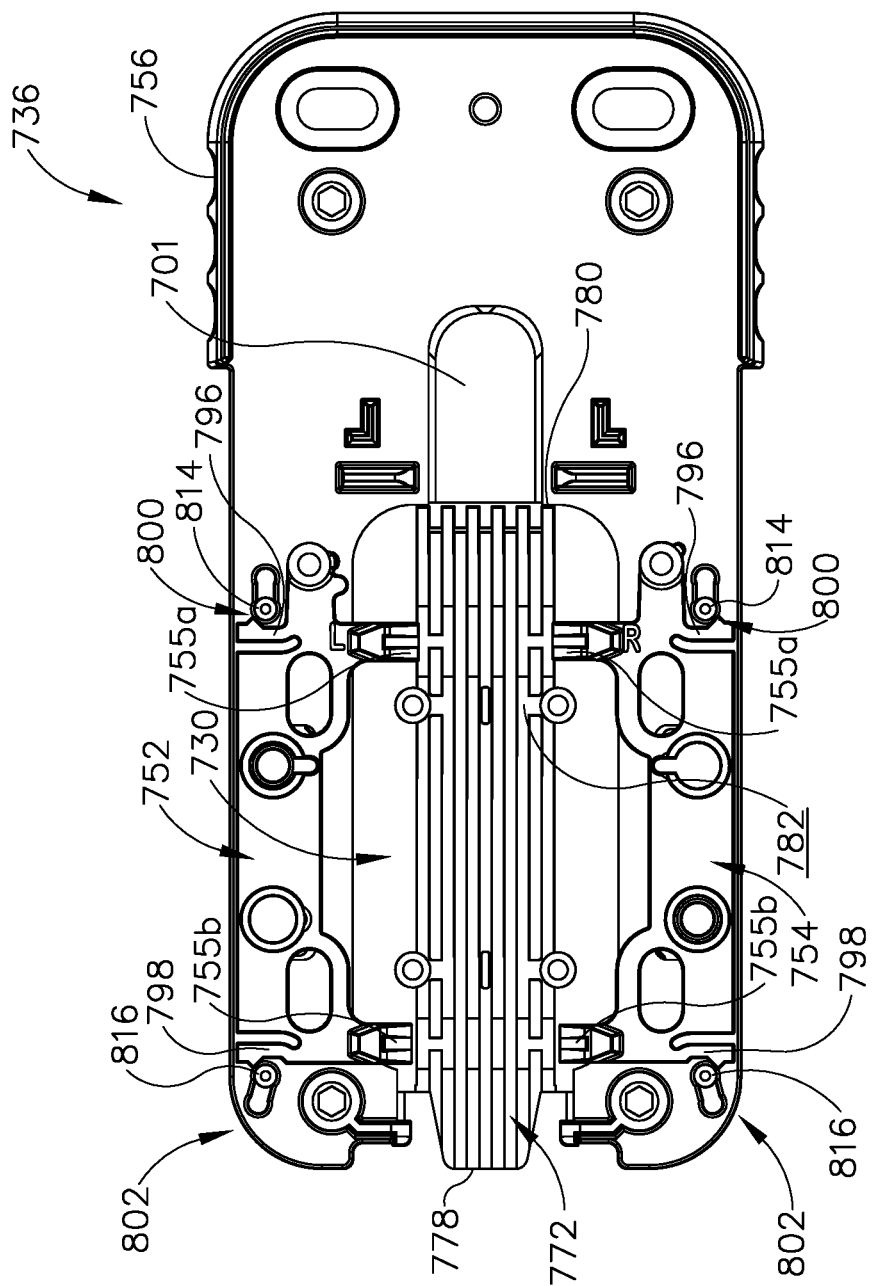
FIG. 33 depicts the top view of the chassis, the platform, and the actuator sleds similar to FIG. 32, but showing the actuator sleds in the release position.

As shown in FIGS. 31-33, left and right actuator sleds (752, 754) are respectively urged outward from the restraint position to the release position away from platform to disengage arms (755*a*, 755*b*) from buttress assemblies (712) on platform (730) as discussed herein. More particularly, distal and proximal detent couplings (800, 802) releasably connect left and right actuator sleds (752, 754) to chassis (736) to arrest movement of left and right actuator sleds (752, 754) in the restraint position and the release position. Distal and proximal detent couplings (800, 802) include distal and proximal cantilever catches (796, 798) extending from each of left and right actuator sleds (752, 754) as discussed briefly above. In addition, distal and proximal detent couplings (800, 802) respectively further include distal and proximal ground cams (814, 816) extending from chassis (736) in respective engagement with distal and proximal cantilever catches (796, 798).

In the restraint position shown in FIG. 31, each distal cantilever catch (796) is respectively engaged with each distal ground cam (814), and each proximal cantilever catch (798) is respectively engaged with each proximal ground cam (816) to urge left and right actuator sleds (752, 754) inward toward the restraint position. Directing left and right actuator sleds (752, 754) outward from the restraint position toward the release position as shown in FIG. 32 resiliently deflects distal and proximal cantilever catches (796, 798) as distal and proximal cantilever catches (796, 798) follow distal and proximal ground cams (814, 816). As distal and proximal cantilever catches (796, 798) pass around distal and proximal ground cams (814, 816), distal and proximal cantilever catches (796, 798) reach a tipping point where distal and proximal cantilever catches (796, 798) urge left and right actuator sleds (752, 754) to the release position shown in FIG. 33. In the release position, each distal cantilever catch (796) is respectively engaged with each distal ground cam (814), and each proximal cantilever catch (798) is respectively engaged with each proximal ground cam (816) to urge left and right actuator sleds (752, 754) outward toward the release position. Thereby, distal and proximal detent couplings (800, 802) effectively hold left and right actuator sleds (752, 754) in the release position to inhibit arms (755*a*, 755*b*) from inadvertently returning inward and catching buttress assembly (712) upon removal of an end effector as discussed herein.

iii. Exemplary Adhesion of Buttress to Surgical Stapler and Cutting of Buttress Assembly with Tissue As noted above, upper and lower buttress assemblies (712) include upper and lower adhesive layers (742) (or other form of adhesive material) to adhere respective buttresses (714) to an underside of an anvil and deck of a staple cartridge of an end effector. Such adhesive may provide proper positioning of buttress (714) before and during actuation of an end effector; then allow buttress (714) to separate from the end effector after the end effector has been actuated, without causing damage to buttress (714) that is substantial enough to compromise the proper subsequent functioning of buttress (714). Buttress assemblies (712) may further incorporate the teachings described in U.S. Pat. App. No. 16/235,473, entitled "Adhesive Distribution on Buttress for Surgical Stapler," filed on Dec. 28, 2018, published as U.S. Pub. No. 2020/0205820 on Jul. 2, 2020, the disclosure of which is hereby incorporated by reference.

By way of example only and not limitation, buttress applier cartridge assembly (710) can be used to apply buttress assemblies (712) with end effector (40) as shown and described with respect to FIGS. 15-18. In such an instance, buttress assemblies (712) are attached with end effector (40) in the same manner as described with buttress assemblies (100, 110). Moreover, other end effectors described herein can be used in place of end effector (40) such that buttress applier cartridge assembly (710) can be used to apply buttress assemblies (712) with to any of those end effectors. As shown and described above, various end effectors may have a straight configuration, a bent or curved tip configuration where the anvil includes a rigid bent or curved tip, or a bent or curved tip configuration where the anvil includes a deformable bent or curve tip. Despite these different configurations, as will be described further below, buttress applier cartridge assembly (710) is configured for use with any such configuration end effector. Furthermore, as mentioned above, buttress applier cartridge assembly (710) is configured to accommodate alternative camber orientations of an end effector, including parallel-camber, over-camber, and under-camber orientations. As mentioned above, pad (772) provides sufficient compression such that adhesive layers (742) of buttresses (714) completely or at least substantially contact the respect parts of the end effector along their longitudinal length to adhere buttresses (712) to the end effector whether the end effector is configured with an over-camber orientation, under-camber orientation, or parallel-camber orientation.

iv. Exemplary Opening Feature Accommodating Curved Tip End Effectors

Referring to buttress applier cartridge (716) as shown in FIGS. 19-33, another feature of buttress applier cartridge (716) pertains to the ability for buttress applier cartridge (716) to be used with a variety of end effectors, including those with a bent or curved tip, which could be as part of the anvil or even as part of the cartridge. In this respect, buttress applier cartridge (716) comprises an opening (701). Opening (701) is configured as a space or void where a portion of an end effector can pass through buttress applier cartridge (716) from a top side or upper side to a bottom side or lower side. As will be described further below, when used with an end effector having a curved tip, opening (701) allows for the jaws of the end effector to be closed with the curved tip passing through opening (701) so that the upper jaw and lower jaw of the end effector can close to at least the point where the upper jaw and lower jaw contact buttress assemblies (712) along its full longitudinal length, or at least substantially along its longitudinal length. At the same time, opening (701) does not impede or hinder the use of straight tip design end effectors.

Referring now to FIGS. 19 and 29-33, in the present example opening (701) is defined by chassis (736) along a distal portion of opening (701) and lateral sides of opening (701). Furthermore, opening is defined by platform (730) along a proximal portion of opening (701). Thus in the present example, multiple structures or components of buttress applier cartridge (716) combine to define opening (701). In some other versions, opening (701) may be defined by fewer, additional, or other components. Also in the present example, opening (701) is defined by chassis (736) and platform (730) such that opening (701) comprises a U-shaped opening. In view of the teachings herein, other ways to define opening (701) to provide for alternate opening shapes will be apparent to those of ordinary skill in the art.

Figure 34:
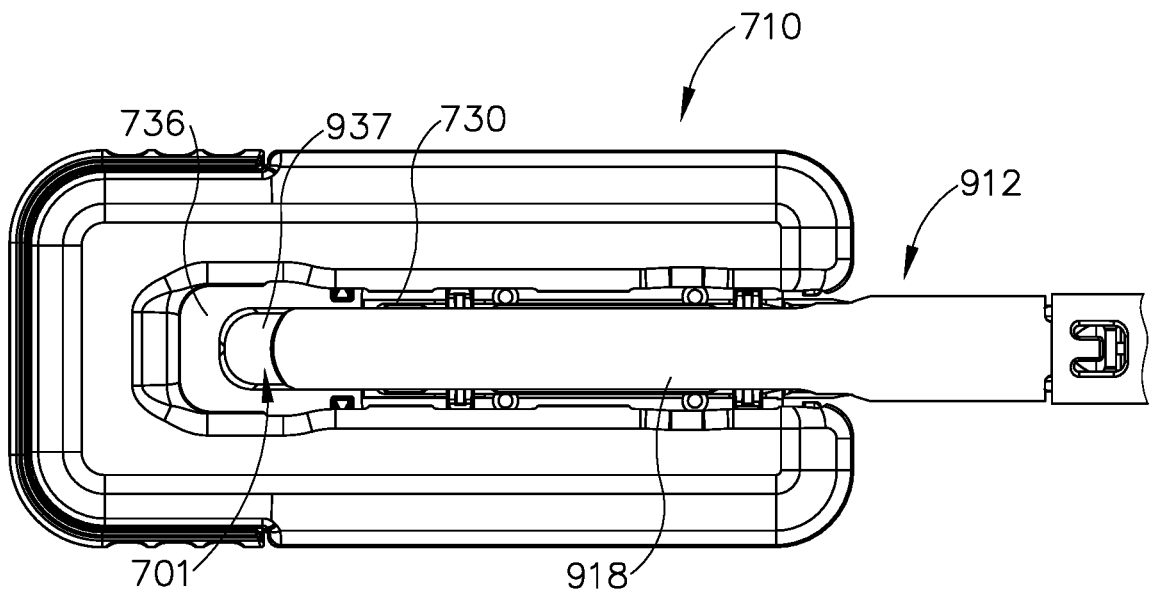
FIG. 34 depicts a top view of an exemplary end effector of a surgical instrument showing the buttress assembly applicator of FIG. 19 positioned between the upper and lower jaws of the end effector in a closed position.
Figure 35:
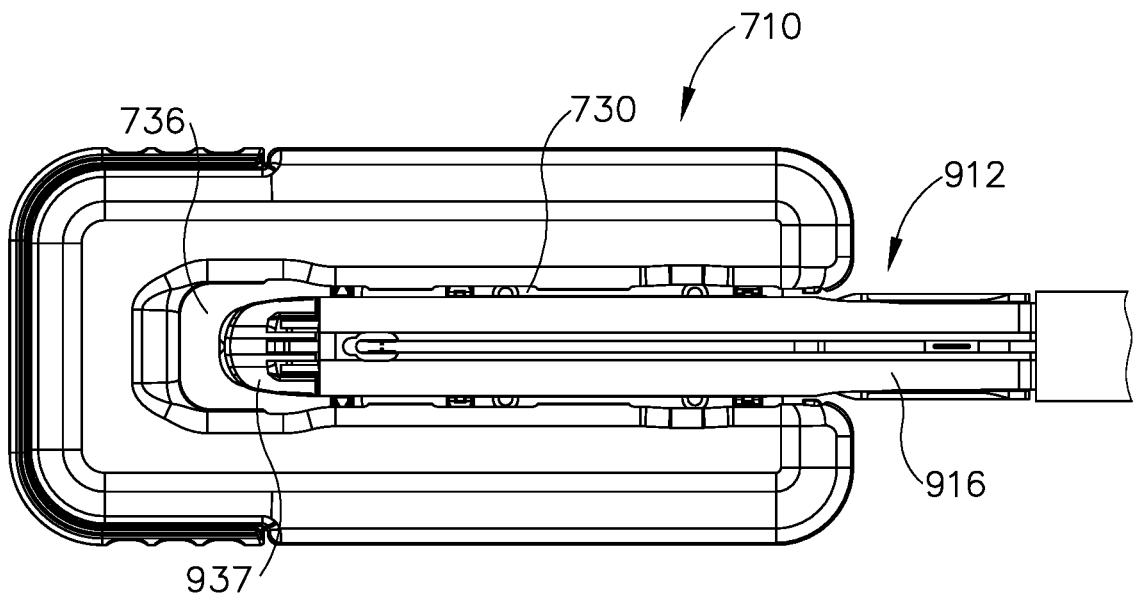
FIG. 35 depicts a bottom view of the end effector of FIG. 34, showing the buttress assembly applicator of FIG. 19 positioned between the upper and lower jaws of the end effector in a closed position.

Referring to FIGS. 34 and 35, buttress applier cartridge assembly (710) is shown used with end effector (912). End effector (912) comprises a straight tip configuration, similar to end effectors (12, 40) described above. End effector (912) comprises anvil (918) and jaw (916) holding a staple cartridge (937). As shown in FIG. 34, when end effector (912) is positioned within buttress applier cartridge assembly (710) and closed, opening (701) reveals a portion of cartridge (937) on the other side of platform (730). This is the case in this example as end effector (912) is configured such that cartridge (937) extends further distally compared to anvil (918) when end effector (912) is closed. As shown in FIG. 35, the view from the other side in this configuration shows that opening (701) is visually blocked by the distal portion of cartridge (937). Nevertheless, buttress applier cartridge assembly (710) is configured for use with straight tipped end effectors such as end effectors (12, 40, 912) described herein, among others.

Figure 36:
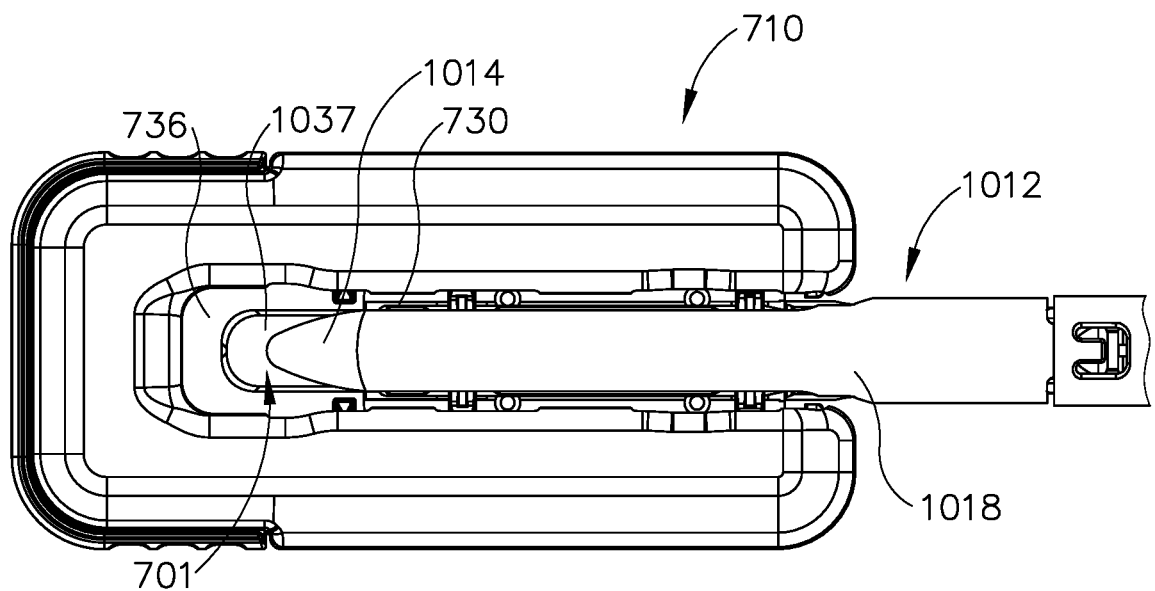
FIG. 36 depicts a top view of an exemplary end effector of a surgical instrument showing the buttress assembly applicator of FIG. 19 positioned between the upper and lower jaws of the end effector in a closed position.
Figure 37:
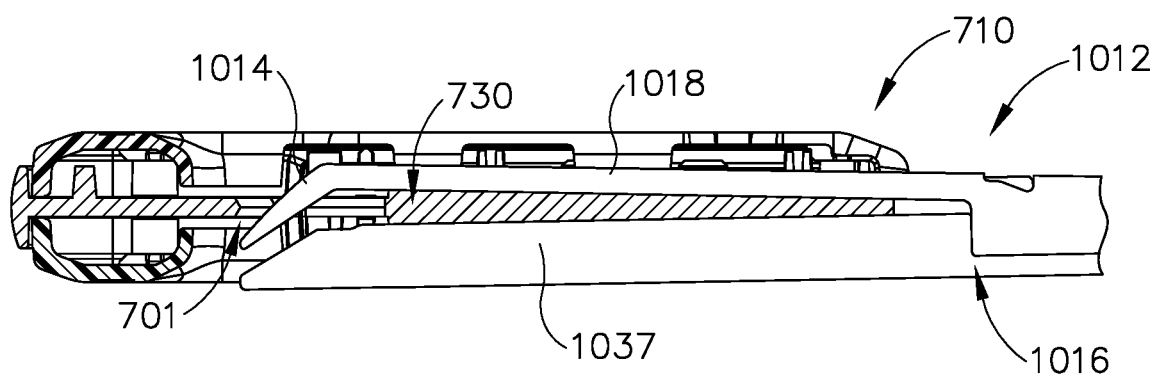
FIG. 37 depicts a side elevation view of the end effector of FIG. 36, showing the buttress assembly applicator of FIG. 19 in cross-section and positioned between the upper and lower jaws of the end effector in a closed position.

Referring to FIGS. 36 and 37, buttress applier cartridge assembly (710) is shown used with end effector (1012). End effector (1012) comprises a bent or curved tip configuration, similar to end effectors (212, 312, 412, 512, 612) described above. End effector (1012) comprises anvil (1018) and jaw (1016) holding a staple cartridge (1037). As shown in FIG. 36, when end effector (1012) is positioned within buttress applier cartridge assembly (710) and closed, opening (701) reveals a portion of cartridge (1037) on the other side of platform (730). This is the case in this example as end effector (1012) is configured such that cartridge (1037) extends further distally compared to anvil (918) when end effector (912) is closed and contacting platform (730). As shown in FIG. 37, with end effector (1012) closed and contacting platform (730), a curved tip (1014) of anvil (1018) passes through opening (701) extending toward cartridge (1037). In the present example, curved tip (1014) is rigid in some versions and deformable in other versions. In either configuration for curved tip (1014), buttress applier cartridge assembly (710) with opening (701) accommodates anvil (1018) and curved tip (1014) such that curved tip (1014) extends through opening (701) when loading buttress assemblies (712) onto end effector (1012).

VII. EXEMPLARY ALTERNATE BUTTRESS APPLIER CARTRIDGE WITH PROXIMAL ALIGNMENT FEATURE AND DISTAL OPENING TO ACCOMMODATE CURVED TIP END EFFECTORS

In other versions of a buttress applier cartridge, an alternate opening, similar to opening (701) described above, can be incorporated into a buttress applier cartridge to accommodate an end effector having a curved tip. Additionally, those buttress applier cartridges described herein can also include one or more alignment features configured to align the end effector of the surgical stapler with the buttress assemblies prior to applying the buttress assemblies to the end effector.

Figure 38:
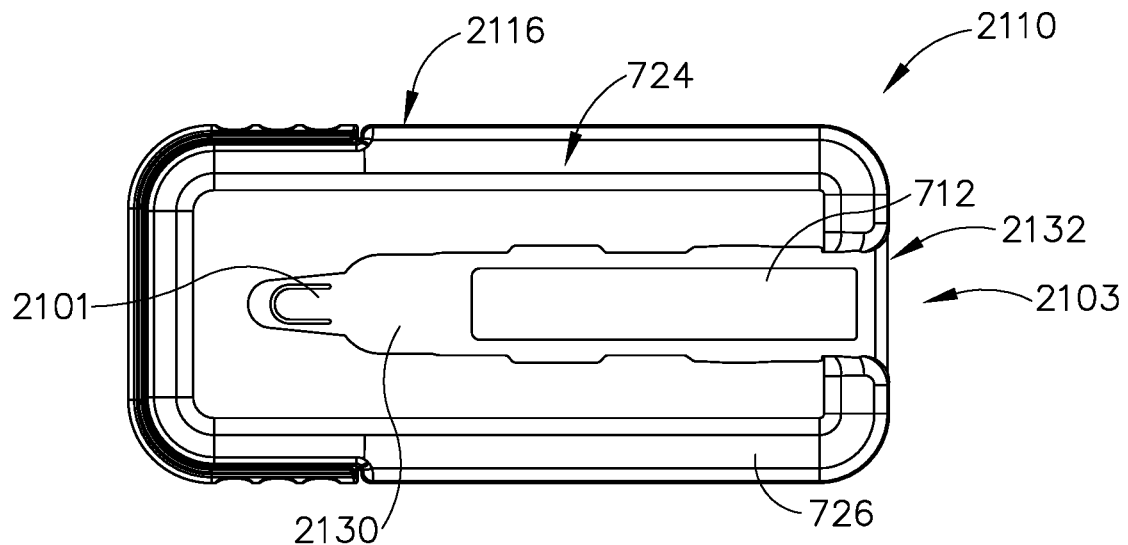
FIG. 38 depicts a top view of another exemplary buttress assembly applicator carrying one or more exemplary buttress assemblies for applying to an end effector of a surgical stapler.
Figure 39:
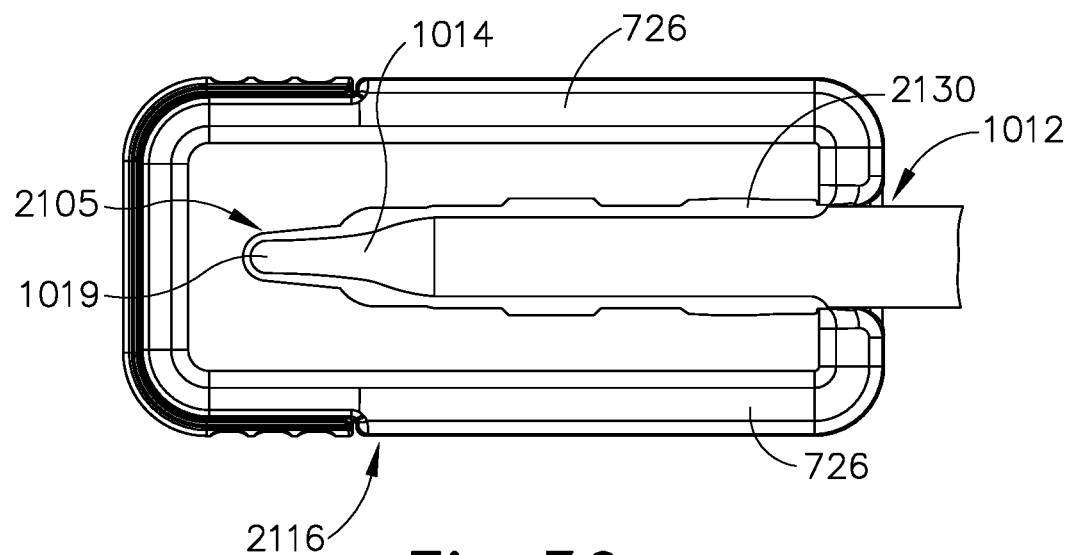
FIG. 39 depicts a top view of the buttress assembly applicator of FIG. 38, shown with an end effector positioned within a channel or space defined by the buttress assembly applicator prior to clamping.
Figure 40:
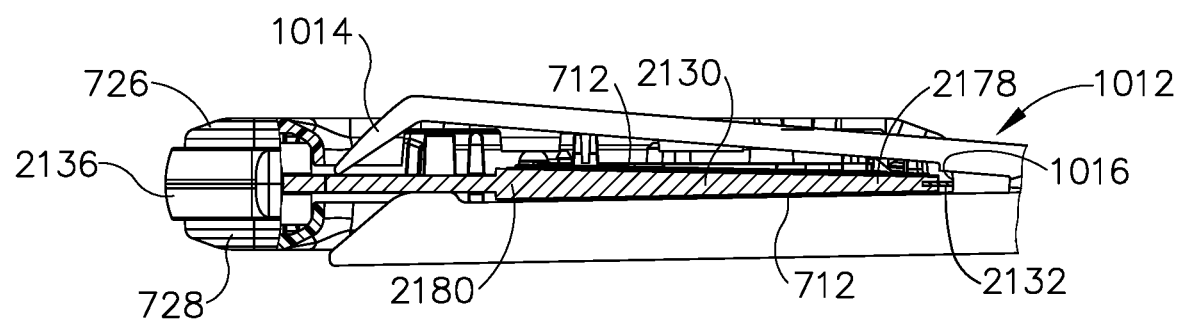
FIG. 40 depicts a side elevation view of the buttress assembly applicator and end effector of FIG. 39, shown with the end effector positioned but not clamped.
Figure 41:
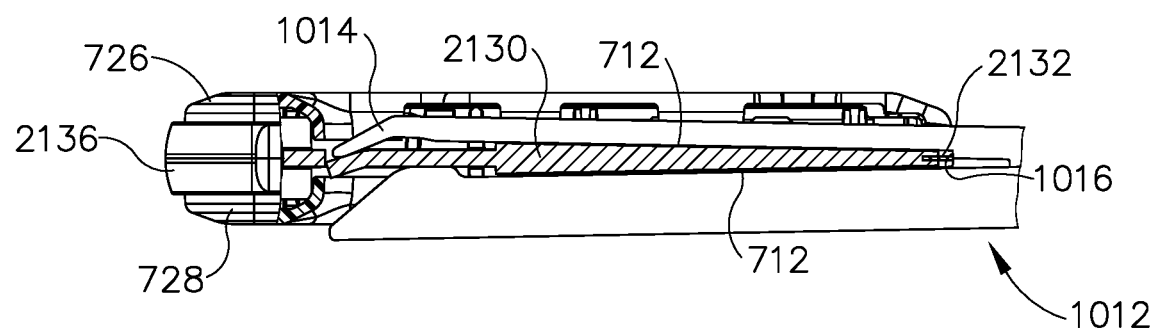
FIG. 41 depicts a side elevation view of the buttress assembly applicator and end effector of FIG. 39, shown with the end effector positioned and in a clamped state.

Referring to FIGS. 38-41, buttress applier cartridge assembly (2110) is shown, which is similar to buttress applier cartridge assembly (710) shown and described above. To that extent, the teachings above with respect to buttress applier cartridge assembly (710) apply equally to buttress applier cartridge assembly (2110) except for the differences described below. Buttress applier cartridge assembly (2110) comprises buttress applier cartridge (2116) having housing assembly (724), which has upper housing (726) and lower housing (728). In the present example, housing assembly (724) defines a channel (2103) that is open at a proximal end and configured to accommodate an end effector, such as end effector (1012) as shown in FIGS. 39 and 41.

Buttress applier cartridge (2116) further comprises chassis (2136) and platform (2130). In some examples similar to the configuration for buttress applier cartridge (716) described above, chassis (2136) is connectable with housing assembly (724), and platform (2130) is connectable with chassis (2136). In this manner platform (2130) is connectable with housing assembly (724) indirectly via chassis (2136). Still in other examples buttress applier cartridges (716, 2116) can be configured such that platform (2136) may be directly connectable with housing assembly (724).

As best seen in FIG. 38, platform (2130) is configured to retain buttress assemblies (712) in the same manner as described above with respect to buttress applier cartridge (716). In the present example, platform (2130) is compressible and also extends proximally to distally such that the space or area defined by channel (2103) is encompassed by platform (2130). Near a distal end of channel (2103), platform (2130) includes opening (2101), which is defined by a hole or cut-out in platform (2130). With this configuration, opening (2101) is located distal to where one or more buttress assemblies (712) are supported or supportable by platform (2130). In the present example, opening (2101) comprises a U-shaped cut-out. In this manner, opening (2101) is formed in platform (2130), and defined on all sides by platform (2130). Similar to opening (701) described above, opening (2101) is configured to allow curved tip (1014) of end effector (1012) or another similar end effector to pass through platform (2130) and/or chassis (2136). In this manner curved tip (1014) extends transversely from one side of combined chassis (2136) and platform (2130) to the other side.

Opening (2101) can be configured to be oversized relative to curved tip (1014), undersized relative to curved tip (1014), or equal or substantially equal in size to curved tip (1014). In some cases, such as with U-shaped opening (2101) described here and shown in FIG. 38, platform (2130) comprises a resilient material such that opening (2101) defined by platform (2130) is expandable, for instance when curved tip (1014) extends through opening (2101) and presses against sides of opening (2101). Also in some cases, such as with U-shaped opening (2101), opening (2101) can be configured with a shape that resembles an outline of the shape of curved tip (1014) of end effector (1012). In this way the shape of opening (2101) and curved tip (1014) of end effector (1012) are complementary. In view of the teachings herein, other configurations for opening (2101) will be apparent to those of ordinary skill in the art.

Similar to platform (730) described above, platform (2130) is configured to be thicker at a distal portion (2180) proximal to opening (2101) compared to a proximal portion (2178) of platform (2130). In this manner platform (2130) comprises a taper from distal portion (2180) to proximal portion (2178). Stated another way, platform (2130) increases in thickness from proximal portion (2178) to distal portion (2180). As shown in the present example of FIG. 38, opening (2101) is located further distally on platform (2130) relative to distal portion (2180). Additionally in the present example, as shown in FIGS. 40 and 41, the portion of platform (2130) with opening (2101) is thinner relative to distal portion (2180).

Referring again to FIG. 39, in defining channel (2103), housing assembly (724) comprises a V-shaped or U-shaped recess (2105) at the distal end of channel (2103). In this manner, recess (2105) is configured to accommodate distal end or distal tip (1019) of curved tip (1014). Referring again to FIG. 38, in the present example, opening (2101) is located within the area defined by recess (2105). In this manner, buttress applier cartridge (2116) is configured to accommodate curved tip (1014) and distal end (1019) at least with features provided on housing assembly (724) and platform (2130). In addition to providing space to accommodate distal end (1019) of curved tip (1014) of end effector (1012), in some instances recess (2105) may further assist in guiding or aligning end effector (1012) when clamping end effector (1012) onto platform (2130) such that end effector (1012) can pick-up buttress assemblies (712). However, as described below, other alignment features or structures can also be provided with buttress applier cartridge (2116) instead of, or in addition to, any alignment provided by recess (2105).

Referring to FIGS. 38, 40, and 41, buttress applier cartridge (2116) also includes an alignment feature (2132) located at a proximal end of buttress applier cartridge (2116). In the present example, alignment feature (2132) comprises a thin rigid portion that extends laterally across the width of channel (2103). In this fashion, alignment features (2132) extends orthogonally relative to the longitudinally extending channel (2103). When end effector (1012) is fully positioned with buttress applier cartridge (2116) as shown in FIG. 40, alignment feature (2132) extends across the cut-line defined by a vertical slot of the end effector where a firing beam travels to sever clamped tissue, the same or similar to vertical slot (49) and firing beam (14) of end effector (12) described above. In some other versions, alignment feature (2132) may extend to a greater or lesser extent laterally across the width of channel (2103) and the cut-line defined by the end effector.

Alignment feature (2132) is configured as a proximal alignment feature. In this way, alignment feature (2132) is configured to engage or contact a proximal edge or one or more tissue stops of the end effector when the end effector is open prior to clamping but fully positioned with buttress applier cartridge (2116) within channel (2103). In some instances, the proximal edge or one or more tissue stops of the end effector may be located on the jaw of the end effector comprising the staple cartridge. In some other instances, the proximal edge or one or more tissue stops of the end effector may be located on the jaw of the end effector comprising the anvil.

Figure 42:
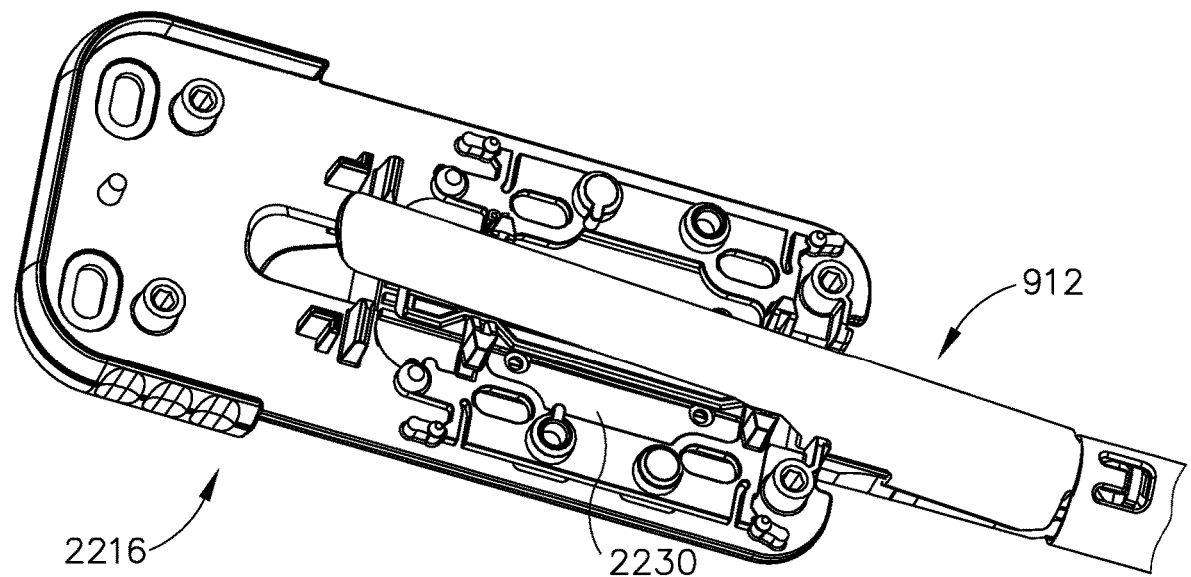
FIG. 42 depicts a perspective view of the buttress assembly applicator of FIG. 38, shown with the housing assembly removed and with an alternate straight tip end effector positioned in an open state over the platform retaining the buttress assemblies.
Figure 43:
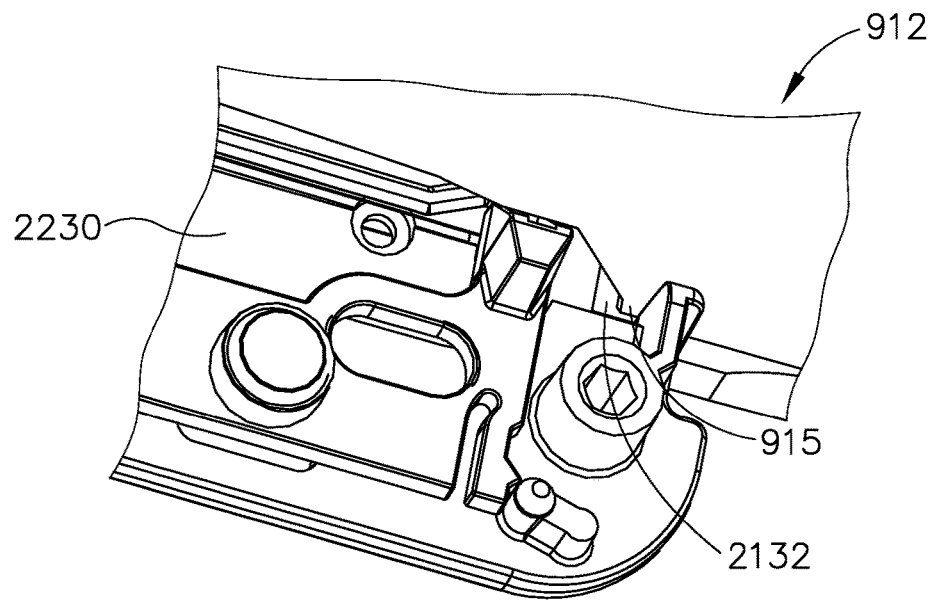
FIG. 43 depicts an enlarged perspective view of a proximal portion of the combined buttress assembly applicator and end effector of FIG. 42.

As shown in FIGS. 40 and 41, alignment feature (2132) is configured to contact proximal edge (1016) of end effector (1012). In some cases, proximal edge (1016) is operable as a tissue stop such that proximal edge (1016) is prevents over inserting tissue within end effector (1012) to ensure a complete cutting and stapling of the target tissue. In other cases, one or more dedicated tissue stops extend from the end effector, and in such cases alignment feature (2132) is configured to contact such tissue stops. Referring to FIGS. 42 and 43, an end effector (912) is shown fully positioned with another buttress applier cartridge (2216), which is shown with housing assembly (724) removed. Alignment feature (2132) is located at the proximal end and extending from platform (2230). Alignment feature (2132) contacts tissue stop (915) as best seen in FIG. 43.

Referring again to FIGS. 40 and 41, alignment feature (2132) is connectable with platform (2130) and extends proximally from platform (2130). Furthermore, as shown in the present example, alignment feature (2132) is thinner than the adjacent part of platform (2130) from which alignment feature (2132) extends. In this way, alignment feature (2132) is configured to not interfere with the end effector clamping onto platform (2130) to pick-up buttress assemblies (712). Additionally as shown, alignment feature (2132) is positioned between where buttress assemblies (712) are supported or supportable by platform (2130). In some versions, alignment feature (2132) comprises a separate rigid structure that connects with platform (2130). However, in other versions, alignment feature (2132) may be a rigid proximal part or end of platform (2130) itself, such that alignment feature (2132) is formed as part of platform (2130).

When an end effector is used with a buttress applier cartridge having alignment feature (2132), alignment feature (2132) guides the end effector to align the end effector relative to the buttress assemblies (712) supported by the buttress applier cartridge. Thus alignment feature (2132) is configured as a proximal alignment feature that aligns a longitudinal position of the end effector, including aligning the distal part of the end effector.

In the illustrated example of FIGS. 39-41 where end effector (1012) is used with buttress applier cartridge assembly (2110), proximal edge (1016) is used to align longitudinal position of end effector (1012) relative to platform (2130) and buttress assemblies (712) supported thereon. Additionally, in the present example, alignment feature (2132) is configured to guide curved tip (1014) of end effector (1012) to align curved tip (1014) with opening (2101). In this way, buttress applier cartridge (2116) is configured so that the spacing between opening (2101) and alignment feature (2132) will allow for curved tip (1014) of end effector (1012) to align with opening (2101) when proximal edge (1016) of end effector (1012) contacts alignment feature (2132) prior to clamping end effector (1012) on platform (2130). Furthermore, when subsequently clamping end effector (1012), the alignment of curved tip (1014) with opening (2101) allows at least a portion of curved tip (1014) to extend through or pass through opening (2101). As shown in FIG. 41, when this occurs, opening (2101) deforms such that the portion of platform (2130) around opening (2101) deflects downward away from curved tip (1014) as curved tip (1014) contacts platform (2130) and pushes platform (2130) downward. In view of the teachings herein, other ways to incorporate one or more alignment features with a buttress applier cartridge that align an end effector of a surgical stapler with the buttress applier cartridge, or ways to modify alignment feature (2132) for use with such an end effector will be apparent to those of ordinary skill in the art.

The various buttress applier cartridges described herein may be used with any of the end effectors described herein. By way of example, and not limitation, those features of the buttress applier cartridges that are configured to work with and/or accommodate an end effector having a curved tip make the buttress applier cartridges suitable for use with end effectors having various styles and configurations for the curved tip. For instance, the buttress applier cartridges described herein with features for a curved tip end effector can be used with end effectors where the curved tip may be gradually curved, or where the curved tip may be non-aligned or at an angle relative to the axis of the anvil such that the curved tip has a more angled or bent configuration rather than gradual curve. Also, the buttress applier cartridges with features to accommodate end effectors with a curved tip described herein can be used with, or configured for use with, end effectors where the curved tip portion is spaced from the distal end of the cartridge or terminates at the same or similar point as the distal end of the cartridge. Also, the buttress applier cartridges with features to accommodate end effectors with a curved tip described herein can be used, or configured for use with, end effectors that have curved tips configured for different uses or applications such as atraumatic tips, dissecting tips, visualization tips, placement tips, deflectable or deformable tips, and combinations thereof, etc. In view of the teachings herein, other ways to configure the buttress applier cartridges described herein to work with the end effectors described herein will be apparent to those of ordinary skill in the art.

VIII. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A buttress applier cartridge is configured to retain one or more buttress assemblies. The buttress applier cartridge is further configured for use with an end effector of a surgical stapler to apply the one or more buttress assemblies to a select one or more of a first jaw and a second jaw of the end effector. The first jaw of the end effector comprises an anvil and the second jaw of the end effector comprises a staple cartridge. The buttress applier cartridge comprises (a) a housing assembly having a proximal end and a distal end. The housing assembly defines a channel extending longitudinally and configured to receive the end effector. The buttress applier cartridge further comprises (b) a platform, directly or indirectly connectable with the housing assembly. The platform extends longitudinally within an area defined by the channel, and is configured to support the one or more buttress assemblies thereon. The buttress applier cartridge further comprises (c) an opening that extends transversely from a first side of the platform to a second side of the platform opposite the first side of the platform. The opening is configured to receive a curved tip of the end effector, allowing at least a portion of the curved tip to extend from the first side of the platform to the second side of the platform. The buttress applier cartridge further comprises (d) an alignment feature connectable with the platform, and extending proximally therefrom. The alignment feature is configured to contact a tissue stop of the end effector when the end effector is fully positioned within the channel defined by the housing assembly.

Example 2

The buttress applier cartridge of Example 1, wherein the alignment feature is rigid.

Example 3

The buttress applier cartridge of any one or more of Example 1 through Example 2, wherein the alignment feature is thinner than the platform.

Example 4

The buttress applier cartridge of any one or more of Example 1 through Example 3, wherein the alignment feature is positioned between where the one or more buttress assemblies that are supportable by the platform.

Example 5

The buttress applier cartridge of any one or more of Example 1 through Example 4, wherein the alignment feature extends orthogonally relative to the longitudinally extending channel such that the alignment feature extends across a cut line defined by the end effector when the end effector is positioned within the channel.

Example 6

The buttress applier cartridge of any one or more of Example 1 through Example 5, wherein the alignment feature connects with a proximal end of the platform.

Example 7

The buttress applier cartridge of any one or more of Example 1 through Example 6, wherein the alignment feature is configured to guide the curved tip of the end effector to align the curved tip of the end effector with the opening.

Example 8

The buttress applier cartridge of any one or more of Example 1 through Example 7, wherein the alignment feature is formed as part of the platform.

Example 9

The buttress applier cartridge of any one or more of Example 1 through Example 8, wherein the platform increases in thickness from a proximal portion to a distal portion.

Example 10

The buttress applier cartridge of any one or more of Example 1 through Example 9, wherein the platform is compressible.

Example 11

The buttress applier cartridge of any one or more of Example 1 through Example 10, further comprising a chassis, wherein the chassis connects with the housing assembly and the platform connects with the chassis.

Example 12

The buttress applier cartridge of any one or more of Example 1 through Example 11, wherein the opening comprises a U-shaped cut-out.

Example 13

The buttress applier cartridge of any one or more of Example 1 through Example 12, wherein the opening is located distal to where the one or more buttress assemblies are supportable by the platform.

Example 14

The buttress applier cartridge of any one or more of Example 1 through Example 13, wherein clamping the end effector on the platform causes the curved tip of the end effector to at least partially extend through the opening.

Example 15

The buttress applier cartridge of any one or more of Example 1 through Example 14, wherein the opening deforms when the curved tip passes through the opening.

Example 16

The buttress applier cartridge of any one or more of Example 1 through Example 15, wherein the opening and alignment feature are spaced such that when the tissue stops of the end effector contact the alignment feature and the end effector is clamped, the curved tip of the end effector aligns with and extends through the opening.

Example 17

The buttress applier cartridge of any one or more of Example 1 through Example 16, further configured such that a proximal edge of a select one of the first jaw and second jaw of the end effector are used to align longitudinal position of the end effector relative to the platform and the one or more buttress assemblies configured to be supported by the platform.

Example 18

The buttress applier cartridge of any one or more of Example 1 through Example 17, wherein the curved tip of the end effector is a dissecting tip.

Example 19

A buttress applier cartridge assembly is configured for use with an end effector of a surgical stapler. The buttress applier cartridge assembly comprises (a) a buttress assembly configured to be selectively adhered the end effector when clamping the end effector on the buttress applier cartridge assembly. The buttress applier cartridge assembly further comprises (b) a buttress applier cartridge selectively retaining the buttress assembly, wherein the buttress applier cartridge comprises (i) a platform extending longitudinally from a proximal portion to a distal portion. The platform is configured to selectively support the buttress assembly, and to receive the end effector. The buttress applier cartridge further comprises (ii) an opening extending transversely from a first side of the platform to a second side of the platform opposite the first side of the platform. The opening is configured to receive a curved tip of the end effector allowing at least a portion of the curved tip to pass through the opening from the first side of the platform to the second side of the platform. The buttress applier cartridge further comprises (iii) an alignment feature located at a proximal end of the buttress applier cartridge and configured to contact a proximal edge of the end effector prior to clamping the end effector on the platform to guide the end effector into alignment with the buttress assembly supported by the platform prior to clamping the end effector.

Example 20

A buttress application system comprises (a) an end effector for a surgical stapler. The end effector comprises a first jaw and a second jaw. The first jaw of the end effector comprises an anvil and the second jaw of the end effector comprises a staple cartridge. The end effector further comprises a curved tip and one or more tissue stops. The buttress application system further comprises (b) a pair of buttress assemblies, each comprising a buttress and an adhesive. A first buttress assembly of the pair of buttress assemblies is configured to be selectively adhered to the first jaw of the end effector, and a second buttress assembly of the pair of buttress assemblies is configured to be selectively adhered to the second jaw of the end effector. The buttress application system further comprises (c) a buttress applier cartridge configured to selectively retain the buttress assemblies and apply the buttress assemblies to the end effector. The buttress applier cartridge comprises (i) a housing defining a channel extending longitudinally. The channel is open at a proximal end and configured to receive the end effector. The buttress applier cartridge further comprises (ii) a platform extending longitudinally and operatively connected to the housing directly or indirectly. The platform supports the buttress assemblies thereon. The buttress applier cartridge further comprises (iii) an opening that extends transversely from a first side of the platform to a second side of the platform opposite the first side of the platform. The opening is configured to receive a curved tip of the end effector when the end effector is clamped onto the platform. The buttress applier cartridge further comprises (iv) an alignment feature connectable with the platform. The alignment feature extends proximally from the platform. The alignment feature is configured to contact the one or more tissue stops of the end effector when the end effector is open and positioned within the channel defined by the housing assembly.

IX. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. Pat. No. D836,198, entitled "Surgical Stapler End Effector with Varying Deck Height and Tissue Gripping Features," issued Dec. 18, 2018, the disclosure of which is incorporated by reference herein. Various suitable ways in which the teachings herein may be combined with the teachings of U.S. Pat. No. D836,198, will be apparent to those of ordinary skill in the art.

It should also be understood that the teachings herein may be readily combined with various teachings in U.S. Pat. No. D833,010, entitled "Circular Surgical Stapler End Effector with Varying Deck Height and Tissue Gripping Features,"

issued Nov. 6, 2018, the disclosure of which is incorporated by reference herein. Various suitable ways in which the teachings herein may be combined with the teachings of U.S. Pat. No. D833,010, will be apparent to those of ordinary skill in the art.

It should also be understood that the teachings herein may be readily combined with various teachings in U.S. Pat. Pub. No. 2018/0235610, entitled "Surgical Stapler with Insertable Distal Anvil Tip," published Aug. 23, 2018, issued as U.S. Pat. No. 10,729,434 on Aug. 4, 2020, the disclosure of which is incorporated by reference herein. Various suitable ways in which the teachings herein may be combined with the teachings of U.S. Pat. Pub. No. 2018/0235610, issued as U.S. Pat. No. 10,729,434 on Aug. 4, 2020, will be apparent to those of ordinary skill in the art.

It should also be understood that the teachings herein may be readily combined with various teachings in U.S. Pat. Pub. No. 2018/0235611, entitled "Surgical Stapler with Cooperating Distal Tip Features on Anvil and Staple Cartridge," published Aug. 23, 2018, the disclosure of which is incorporated by reference herein. Various suitable ways in which the teachings herein may be combined with the teachings of U.S. Pat. Pub. No. 2018/0235611, will be apparent to those of ordinary skill in the art.

It should also be understood that the teachings herein may be readily combined with various teachings in U.S. Pat. No. D836,199, entitled "Surgical Stapler with Bent Anvil Tip and Angled Staple Cartridge Tip," issued Dec. 18, 2018, the disclosure of which is incorporated by reference herein. Various suitable ways in which the teachings herein may be combined with the teachings of U.S. Pat. No. D836,199, will be apparent to those of ordinary skill in the art.

It should also be understood that the teachings herein may be readily combined with various teachings in U.S. Pat. Pub. No. 2018/0235619, entitled "Surgical Stapler with Bent Anvil Tip, Angled Staple Cartridge Tip, and Tissue Gripping Features," published Aug. 23, 2018, issued as U.S. Pat. No. 10,758,231 on Sep. 1, 2020, the disclosure of which is incorporated by reference herein. Various suitable ways in which the teachings herein may be combined with the teachings of U.S. Pat. Pub. No. 2018/0235619, issued as U.S. Pat. No. 10,758,231 on Sep. 1, 2020, will be apparent to those of ordinary skill in the art.

It should also be understood that the teachings herein may be readily combined with various teachings in U.S. patent application Ser. No. 16/035,893, entitled "Method of Surgical Stapling with End Effector Component Having a Curved Tip," filed Jul. 16, 2018, the disclosure of which is incorporated by reference herein. Various suitable ways in which the teachings herein may be combined with the teachings of U.S. patent application Ser. No. 16/035,893, published as U.S. Pat. No. 2019/0000481 on Jul. 3, 2019, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System, issued Sep. 30, 2014, the disclosure of which is incorporated by reference herein; U.S. Pat. No. 8,820,605, entitled "Robotically-Controlled Surgical Instrument with Force-Feedback Capabilities," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable- Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress applier cartridge configured to retain one or more buttress assemblies, wherein the buttress applier cartridge is further configured for use with an end effector of a surgical stapler to apply the one or more buttress assemblies to a select one or more of a first jaw and a second jaw of the end effector, wherein the first jaw of the end effector comprises an anvil and the second jaw of the end effector comprises a staple cartridge, wherein the buttress applier cartridge comprises:
   (a) a housing assembly having a proximal end and a distal end, wherein the housing assembly defines a channel extending longitudinally and configured to receive the end effector;
   (b) a platform, directly or indirectly connectable with the housing assembly, wherein the platform extends longitudinally within an area defined by the channel, wherein the platform is configured to support the one or more buttress assemblies thereon;
   (c) an opening that extends transversely from a first side of the platform to a second side of the platform opposite the first side of the platform, wherein the opening is configured to receive a curved tip of the end effector allowing at least a portion of the curved tip to extend from the first side of the platform to the second side of the platform; and
   (d) an alignment feature, wherein the alignment feature is connectable with the platform and extends proximally therefrom, wherein the alignment feature is configured to contact a tissue stop of the end effector when the end effector is fully positioned within the channel defined by the housing assembly.

2. The buttress applier cartridge of claim 1, wherein the alignment feature is rigid.

3. The buttress applier cartridge of claim 1, wherein the alignment feature is thinner than the platform.

4. The buttress applier cartridge of claim 1, wherein the alignment feature is positioned between where the one or more buttress assemblies that are supportable by the platform.

5. The buttress applier cartridge of claim 1, wherein the alignment feature extends orthogonally relative to the longitudinally extending channel such that the alignment feature extends across a cut line defined by the end effector when the end effector is positioned within the channel.

6. The buttress applier cartridge of claim 1, wherein the alignment feature connects with a proximal end of the platform.

7. The buttress applier cartridge of claim 1, wherein the alignment feature is configured to guide the curved tip of the end effector to align the curved tip of the end effector with the opening.

8. The buttress applier cartridge of claim 1, wherein the alignment feature is formed as part of the platform.

9. The buttress applier cartridge of claim 1, wherein the platform increases in thickness from a proximal portion to a distal portion.

10. The buttress applier cartridge of claim 1, wherein the platform is compressible.

11. The buttress applier cartridge of claim 1, further comprising a chassis, wherein the chassis connects with the housing assembly and the platform connects with the chassis.

12. The buttress applier cartridge of claim 1, wherein the opening comprises a U-shaped cut-out.

13. The buttress applier cartridge of claim 1, wherein the opening is located distal to where the one or more buttress assemblies are supportable by the platform.

14. The buttress applier cartridge of claim 1, wherein clamping the end effector on the platform causes the curved tip of the end effector to at least partially extend through the opening.

15. The buttress applier cartridge of claim 1, wherein the opening deforms when the curved tip passes through the opening.

16. The buttress applier cartridge of claim 1, wherein the opening and alignment feature are spaced such that when the tissue stops of the end effector contact the alignment feature and the end effector is clamped, the curved tip of the end effector aligns with and extends through the opening.

17. The buttress applier cartridge of claim 1, further configured such that a proximal edge of a select one of the first jaw and second jaw of the end effector are used to align longitudinal position of the end effector relative to the platform and the one or more buttress assemblies configured to be supported by the platform.

18. The buttress applier cartridge of claim 1, wherein the curved tip of the end effector is a dissecting tip.

19. A buttress applier cartridge assembly configured for use with an end effector of a surgical stapler, wherein the buttress applier cartridge assembly comprises:
- (a) a buttress assembly configured to be selectively adhered the end effector when clamping the end effector on the buttress applier cartridge assembly; and
- (b) a buttress applier cartridge selectively retaining the buttress assembly, wherein the buttress applier cartridge comprises:
  - (i) a platform extending longitudinally from a proximal portion to a distal portion, wherein the platform is configured to selectively support the buttress assembly, wherein the platform is further configured to receive the end effector,
  - (ii) an opening extending transversely from a first side of the platform to a second side of the platform opposite the first side of the platform, wherein the opening is configured to receive a curved tip of the end effector allowing at least a portion of the curved tip to pass through the opening from the first side of the platform to the second side of the platform, and
  - (iii) an alignment feature located at a proximal end of the buttress applier cartridge and configured to contact a proximal edge of the end effector prior to clamping the end effector on the platform to guide the end effector into alignment with the buttress assembly supported by the platform prior to clamping the end effector.

20. A buttress application system comprising:
- (a) an end effector for a surgical stapler, wherein the end effector comprises a first jaw and a second jaw, wherein the first jaw of the end effector comprises an anvil and the second jaw of the end effector comprises a staple cartridge, wherein the end effector further comprises a curved tip and one or more tissue stops;
- (b) a pair of buttress assemblies, each comprising a buttress and an adhesive, wherein a first buttress assembly of the pair of buttress assemblies is configured to be selectively adhered to the first jaw of the end effector, and wherein a second buttress assembly of the pair of buttress assemblies is configured to be selectively adhered to the second jaw of the end effector; and
- (c) a buttress applier cartridge configured to selectively retain the buttress assemblies and apply the buttress assemblies to the end effector, wherein the buttress applier cartridge comprises:
  - (i) a housing defining a channel extending longitudinally, wherein the channel is open at a proximal end and configured to receive the end effector,
  - (ii) a platform extending longitudinally and operatively connected to the housing directly or indirectly, wherein the platform supports the buttress assemblies thereon,
  - (iii) an opening that extends transversely from a first side of the platform to a second side of the platform opposite the first side of the platform, wherein the opening is configured to receive a curved tip of the end effector when the end effector is clamped onto the platform, and
  - (iv) an alignment feature connectable with the platform, wherein the alignment feature extends proximally from the platform, wherein the alignment feature is configured to contact the one or more tissue stops of the end effector when the end effector is open and positioned within the channel defined by the housing assembly.

\* \* \* \* \*